United States Patent
Brögmann et al.

(10) Patent No.: US 10,420,762 B2
(45) Date of Patent: *Sep. 24, 2019

(54) PHARMACEUTICAL PREPARATION CONTAINING OXYCODONE AND NALOXONE

(71) Applicant: Purdue Pharma L.P., Stamford, CT (US)

(72) Inventors: Bianca Brögmann, Ulm (DE); Silke Mühlau, Biberach (DE); Christof Spitzley, Elbtal (DE)

(73) Assignee: Purdue Pharma L.P., Stamford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/881,459

(22) Filed: Jan. 26, 2018

(65) Prior Publication Data
US 2018/0214443 A1 Aug. 2, 2018

Related U.S. Application Data

(63) Continuation of application No. 15/399,487, filed on Jan. 5, 2017, now Pat. No. 9,907,793, which is a continuation of application No. 14/305,785, filed on Jun. 16, 2014, now Pat. No. 9,555,000, which is a continuation of application No. 14/058,068, filed on Oct. 18, 2013, now abandoned, which is a continuation of application No. 13/251,172, filed on Sep. 30, 2011, now abandoned, which is a continuation of application No. 10/510,674, filed as application No. PCT/EP03/03540 on Apr. 4, 2003, now abandoned.

(30) Foreign Application Priority Data

Apr. 5, 2002 (DE) .................................. 102 15 067
Apr. 5, 2002 (DE) .................................. 102 15 131

(51) Int. Cl.
| | |
|---|---|
| *A61K 9/00* | (2006.01) |
| *A61K 31/485* | (2006.01) |
| *A61K 9/16* | (2006.01) |
| *A61K 9/70* | (2006.01) |
| *A61K 9/20* | (2006.01) |

(52) U.S. Cl.
CPC .......... *A61K 31/485* (2013.01); *A61K 9/0053* (2013.01); *A61K 9/1617* (2013.01); *A61K 9/1652* (2013.01); *A61K 9/2009* (2013.01); *A61K 9/2013* (2013.01); *A61K 9/2054* (2013.01); *A61K 9/2077* (2013.01); *A61K 9/2095* (2013.01); *A61K 9/70* (2013.01); *Y10S 514/81* (2013.01); *Y10S 514/812* (2013.01)

(58) Field of Classification Search
None
See application file for complete search history.

(56) References Cited

U.S. PATENT DOCUMENTS

| | | |
|---|---|---|
| 2,770,569 A | 11/1956 | Fromherz et al. |
| 3,133,132 A | 5/1964 | Loeb et al. |
| 3,173,876 A | 3/1965 | Zobrist |
| 3,173,877 A | 3/1965 | Jackson et al. |
| 3,276,586 A | 10/1966 | Rosaen |
| 3,332,950 A | 7/1967 | Blumberg et al. |
| 3,493,657 A | 2/1970 | Lewenstein et al. |
| 3,541,005 A | 11/1970 | Strathmann et al. |
| 3,541,006 A | 11/1970 | Bixler et al. |
| 3,546,876 A | 12/1970 | Fokker et al. |
| 3,676,557 A | 7/1972 | Lachman et al. |
| 3,773,955 A | 11/1973 | Patcher et al. |
| 3,845,770 A | 11/1974 | Theeuwes et al. |
| 3,879,555 A | 4/1975 | Pachter et al. |
| 3,916,889 A | 11/1975 | Russell |
| 3,916,899 A | 11/1975 | Theeuwes et al. |
| 3,950,508 A | 4/1976 | Mony et al. |
| 3,965,256 A | 6/1976 | Leslie |
| 3,966,940 A | 6/1976 | Patcher et al. |
| 4,063,064 A | 12/1977 | Saunders et al. |
| 4,088,864 A | 5/1978 | Theeuwes et al. |
| 4,126,684 A | 11/1978 | Robson et al. |
| 4,160,020 A | 7/1979 | Ayer et al. |
| 4,176,186 A | 11/1979 | Goldberg |
| 4,200,098 A | 4/1980 | Ayer et al. |
| 4,216,314 A | 8/1980 | Raabe et al. |
| 4,237,140 A | 12/1980 | Dudzinski |
| 4,285,987 A | 8/1981 | Ayer et al. |
| 4,293,539 A | 10/1981 | Ludwig et al. |

(Continued)

FOREIGN PATENT DOCUMENTS

| | | |
|---|---|---|
| AU | 200205559 | 11/2002 |
| CA | 2382648 | 3/2001 |

(Continued)

OTHER PUBLICATIONS

Abdulla et al., "Axotomy reduces the effect of analgesic opioids yet increases the effect of nociceptin on dorsal root ganglion neurons"; J of Neuro Sci (1998) vol. 18, pp. 9685-9694.

(Continued)

*Primary Examiner* — Robert A Wax
*Assistant Examiner* — Caralynne E Helm
(74) *Attorney, Agent, or Firm* — Purdue Pharma L.P.; Alan L. Koller; Weiying Yang

(57) ABSTRACT

The invention concerns a storage stable pharmaceutical preparation comprising oxycodone and naloxone for use in pain therapy, with the active compounds being released from the preparation in a sustained, invariant and independent manner.

20 Claims, 9 Drawing Sheets

(56) References Cited

U.S. PATENT DOCUMENTS

| | | |
|---|---|---|
| 4,366,310 A | 12/1982 | Leslie |
| 4,401,672 A | 8/1983 | Portoghese et al. |
| 4,443,428 A | 4/1984 | Oshlack et al. |
| 4,451,470 A | 5/1984 | Ganti |
| 4,457,933 A | 7/1984 | Gordon et al. |
| 4,464,378 A | 8/1984 | Hussain et al. |
| 4,573,995 A | 3/1986 | Chen et al. |
| 4,582,835 A | 4/1986 | Lewis et al. |
| 4,608,376 A | 8/1986 | Pasternak |
| 4,661,492 A | 4/1987 | Lewis et al. |
| 4,668,685 A | 5/1987 | Shami |
| 4,719,215 A | 1/1988 | Goldberg |
| 4,722,928 A | 2/1988 | Boswell et al. |
| 4,730,048 A | 3/1988 | Portoghese et al. |
| 4,760,069 A | 7/1988 | Rzeszotarski et al. |
| 4,769,372 A | 9/1988 | Kreek |
| 4,785,000 A | 11/1988 | Kreek et al. |
| 4,803,208 A | 2/1989 | Pasternak |
| 4,806,341 A | 2/1989 | Chien et al. |
| 4,806,543 A | 2/1989 | Choi |
| 4,806,558 A | 2/1989 | Wuest et al. |
| 4,828,836 A | 5/1989 | Elger et al. |
| 4,834,965 A | 5/1989 | Martani et al. |
| 4,834,984 A | 5/1989 | Goldie et al. |
| 4,834,985 A | 5/1989 | Elger et al. |
| 4,844,907 A | 7/1989 | Elger et al. |
| 4,844,909 A | 7/1989 | Goldie et al. |
| 4,844,910 A | 7/1989 | Leslie et al. |
| 4,861,598 A | 8/1989 | Oshlack |
| 4,861,781 A | 8/1989 | Goldberg |
| 4,867,985 A | 9/1989 | Heafield et al. |
| 4,873,076 A | 10/1989 | Fishman et al. |
| 4,882,335 A | 11/1989 | Sinclair |
| 4,889,860 A | 12/1989 | Rzeszotarski et al. |
| 4,935,428 A | 6/1990 | Lewis |
| 4,940,587 A | 7/1990 | Jenkins et al. |
| 4,957,681 A | 9/1990 | Klimesch et al. |
| 4,970,075 A | 11/1990 | Oshlak |
| 4,987,136 A | 1/1991 | Kreek et al. |
| 4,990,341 A | 2/1991 | Goldie et al. |
| 5,071,646 A | 12/1991 | Malkowska et al. |
| 5,075,341 A | 12/1991 | Mendelson et al. |
| 5,086,058 A | 2/1992 | Sinclair et al. |
| 5,091,189 A | 2/1992 | Heafield et al. |
| 5,096,715 A | 3/1992 | Sinclair |
| 5,102,887 A | 4/1992 | Goldberg |
| 5,130,311 A | 7/1992 | Guillaumet et al. |
| 5,149,538 A | 9/1992 | Granger et al. |
| 5,215,758 A | 6/1993 | Krishnamurthy |
| 5,225,440 A | 7/1993 | London et al. |
| 5,236,714 A | 8/1993 | Lee et al. |
| 5,256,669 A | 10/1993 | Askanazi et al. |
| 5,266,331 A | 11/1993 | Oshlack et al. |
| 5,273,760 A | 12/1993 | Oshlack et al. |
| 5,286,493 A | 2/1994 | Oshlack et al. |
| 5,316,759 A | 5/1994 | Rose et al. |
| 5,317,022 A | 5/1994 | Borsodi et al. |
| 5,321,012 A | 6/1994 | Mayer et al. |
| 5,324,351 A | 6/1994 | Oshlack et al. |
| 5,336,691 A | 8/1994 | Raffa et al. |
| 5,352,680 A | 10/1994 | Portoghese et al. |
| 5,352,683 A | 10/1994 | Mayer et al. |
| 5,356,467 A | 10/1994 | Oshlack et al. |
| 5,356,900 A | 10/1994 | Bihari et al. |
| 5,376,662 A | 12/1994 | Ockert |
| 5,409,944 A | 4/1995 | Black et al. |
| 5,411,745 A | 5/1995 | Oshlack et al. |
| 5,426,112 A | 6/1995 | Zagon et al. |
| 5,436,265 A | 7/1995 | Black et al. |
| 5,457,208 A | 10/1995 | Portoghese et al. |
| 5,460,826 A | 10/1995 | Merrill et al. |
| 5,472,712 A | 12/1995 | Oshlack et al. |
| 5,472,943 A | 12/1995 | Crain et al. |
| 5,474,995 A | 12/1995 | Ducharme et al. |
| 5,478,577 A | 12/1995 | Sackler et al. |
| 5,486,362 A | 1/1996 | Kitchell et al. |
| 5,500,227 A | 3/1996 | Oshlack et al. |
| 5,502,058 A | 3/1996 | Mayer et al. |
| 5,508,042 A | 4/1996 | Oshlack et al. |
| 5,508,043 A | 4/1996 | Krishnamurthy |
| 5,510,368 A | 4/1996 | Lau et al. |
| 5,512,578 A | 4/1996 | Crain et al. |
| 5,514,680 A | 5/1996 | Weber et al. |
| 5,521,213 A | 5/1996 | Prasit et al. |
| 5,534,492 A | 7/1996 | Aston et al. |
| 5,536,752 A | 7/1996 | Ducharme et al. |
| 5,549,912 A | 8/1996 | Oshlack et al. |
| 5,550,142 A | 8/1996 | Ducharme et al. |
| 5,552,422 A | 9/1996 | Gauthier et al. |
| 5,556,838 A | 9/1996 | Mayer et al. |
| 5,574,052 A | 11/1996 | Rose et al. |
| 5,578,725 A | 11/1996 | Portoghese et al. |
| 5,580,578 A | 12/1996 | Oshlack et al. |
| 5,580,876 A | 12/1996 | Crain et al. |
| 5,585,348 A | 12/1996 | Crain et al. |
| 5,591,452 A | 1/1997 | Miller et al. |
| 5,592,310 A | 1/1997 | Sugiura et al. |
| 5,593,994 A | 1/1997 | Batt et al. |
| 5,601,845 A | 2/1997 | Buxton et al. |
| 5,604,253 A | 2/1997 | Lau et al. |
| 5,604,260 A | 2/1997 | Guay et al. |
| 5,616,601 A | 4/1997 | Khanna et al. |
| 5,622,722 A | 4/1997 | Knott et al. |
| 5,624,932 A | 4/1997 | Qin et al. |
| 5,633,259 A | 5/1997 | Qin et al. |
| 5,639,476 A | 6/1997 | Oshlack et al. |
| 5,639,780 A | 6/1997 | Lau et al. |
| 5,656,295 A | 8/1997 | Oshlack et al. |
| 5,670,172 A | 9/1997 | Buxton et al. |
| 5,672,360 A | 9/1997 | Sackler et al. |
| 5,681,585 A | 10/1997 | Oshlack et al. |
| 5,692,500 A | 12/1997 | Gaston-Johansson |
| 5,763,452 A | 6/1998 | Miller et al. |
| 5,767,125 A | 6/1998 | Crain et al. |
| 5,780,479 A | 7/1998 | Kim |
| 5,811,126 A | 9/1998 | Krishnamurthy |
| 5,834,477 A | 11/1998 | Mioduszewski |
| 5,843,480 A | 12/1998 | Miller et al. |
| 5,849,240 A | 12/1998 | Miller et al. |
| 5,858,017 A | 1/1999 | Demopulos et al. |
| 5,860,950 A | 1/1999 | Demopulos et al. |
| 5,866,154 A | 2/1999 | Bahal et al. |
| 5,866,164 A | 2/1999 | Kucznski et al. |
| 5,869,097 A | 2/1999 | Wong et al. |
| 5,879,705 A | 3/1999 | Heafield et al. |
| 5,880,132 A | 3/1999 | Hill |
| 5,891,471 A | 4/1999 | Miller et al. |
| 5,908,848 A | 6/1999 | Miller et al. |
| 5,942,241 A | 8/1999 | Chasin et al. |
| 5,958,452 A | 9/1999 | Oshlack et al. |
| 5,958,458 A | 9/1999 | Norling et al. |
| 5,958,459 A | 9/1999 | Chasin et al. |
| 5,965,161 A | 10/1999 | Oshlack et al. |
| 5,965,163 A | 10/1999 | Miller et al. |
| 5,968,547 A | 10/1999 | Reder et al. |
| 5,968,551 A | 10/1999 | Oshlack et al. |
| 5,972,310 A | 10/1999 | Sachetto |
| 5,972,954 A | 10/1999 | Foss |
| 5,998,434 A | 12/1999 | Mitch et al. |
| 6,024,982 A | 2/2000 | Oshlack et al. |
| 6,068,855 A | 5/2000 | Leslie et al. |
| 6,077,532 A | 6/2000 | Malkowska et al. |
| 6,077,533 A | 6/2000 | Oshlack et al. |
| 6,096,756 A | 8/2000 | Crain et al. |
| 6,103,258 A | 8/2000 | Simon |
| 6,103,261 A | 8/2000 | Chasin et al. |
| 6,114,326 A | 9/2000 | Schueler |
| 6,143,322 A | 11/2000 | Sackler et al. |
| 6,143,328 A | 11/2000 | Heafield et al. |
| 6,159,501 A | 12/2000 | Skinhoj et al. |
| 6,162,467 A | 12/2000 | Miller et al. |
| 6,194,382 B1 | 2/2001 | Crain et al. |
| 6,207,142 B1 | 3/2001 | Odds et al. |
| 6,210,714 B1 | 4/2001 | Oshlack et al. |

(56) References Cited

U.S. PATENT DOCUMENTS

| | | |
|---|---|---|
| 6,228,863 B1 | 5/2001 | Palermo et al. |
| 6,254,887 B1 | 7/2001 | Miller et al. |
| 6,258,042 B1 | 7/2001 | Factor et al. |
| 6,261,599 B1 | 7/2001 | Oshlack et al. |
| 6,277,384 B1 | 8/2001 | Kaiko et al. |
| 6,294,195 B1 | 9/2001 | Oshlack et al. |
| 6,306,438 B1 | 10/2001 | Oshlack et al. |
| 6,310,072 B1 | 10/2001 | Smith et al. |
| 6,316,027 B1 | 11/2001 | Johnson et al. |
| 6,326,027 B1 | 12/2001 | Miller et al. |
| 6,335,033 B2 | 1/2002 | Oshlack et al. |
| 6,362,194 B1 | 3/2002 | Crain et al. |
| 6,375,957 B1 | 4/2002 | Kaiko et al. |
| 6,387,404 B2 | 5/2002 | Oshlack et al. |
| 6,395,705 B2 | 5/2002 | Crain et al. |
| 6,399,096 B1 | 6/2002 | Miller et al. |
| 6,419,959 B1 | 7/2002 | Walter et al. |
| 6,451,806 B2 | 9/2002 | Farrar et al. |
| 6,475,494 B2 | 11/2002 | Kaiko et al. |
| 6,579,536 B1 | 6/2003 | Hirsch et al. |
| 6,596,900 B2 | 7/2003 | Blakemore et al. |
| 6,602,868 B2 | 8/2003 | McBrinn et al. |
| 6,627,635 B2 | 9/2003 | Palermo et al. |
| 6,696,066 B2 | 2/2004 | Kaiko et al. |
| 6,696,088 B2 | 2/2004 | Oshlack et al. |
| 6,706,281 B2 | 3/2004 | Oshlack et al. |
| 6,716,449 B2 | 4/2004 | Oshlack et al. |
| 6,743,442 B2 | 6/2004 | Oshlack et al. |
| 6,765,010 B2 | 7/2004 | Crain et al. |
| 7,172,767 B2 | 2/2007 | Kaiko et al. |
| 7,332,182 B2 | 2/2008 | Sackler |
| 7,419,686 B2 | 9/2008 | Kaiko et al. |
| 7,637,906 B2 | 12/2009 | Koop et al. |
| 7,749,542 B2 | 7/2010 | Kaiko et al. |
| 8,105,631 B2 | 1/2012 | Kaiko et al. |
| 2001/0006967 A1 | 7/2001 | Crain et al. |
| 2001/0018413 A1 | 8/2001 | Crain et al. |
| 2001/0053777 A1 | 12/2001 | Brecht |
| 2002/0006964 A1 | 1/2002 | Young et al. |
| 2002/0010127 A1 | 1/2002 | Oshlack et al. |
| 2002/0031552 A1 | 3/2002 | McTeigue et al. |
| 2003/0004177 A1 | 1/2003 | Kao et al. |
| 2003/0044458 A1 | 3/2003 | Wright, IV et al. |
| 2003/0065002 A1 | 4/2003 | Caruso et al. |
| 2003/0069263 A1 | 4/2003 | Breder et al. |
| 2003/0073714 A1 | 4/2003 | Breder et al. |
| 2003/0092759 A1 | 5/2003 | Abuzzahab, Sr. |
| 2003/0118641 A1 | 6/2003 | Maloney et al. |
| 2003/0124185 A1 | 7/2003 | Oshlack et al. |
| 2003/0143269 A1 | 7/2003 | Oshlack et al. |
| 2003/0178031 A1 | 9/2003 | DuPen et al. |
| 2003/0191147 A1 | 10/2003 | Sherman et al. |
| 2003/0229111 A1 | 12/2003 | Oshlack et al. |
| 2004/0052731 A1 | 3/2004 | Hirsh et al. |
| 2004/0092542 A1 | 5/2004 | Oshlack et al. |
| 2004/0186121 A1 | 9/2004 | Oshlack et al. |
| 2005/0063909 A1 | 3/2005 | Wright et al. |
| 2005/0095291 A1 | 5/2005 | Oshlack et al. |
| 2005/0163856 A1 | 7/2005 | Maloney et al. |
| 2005/0181046 A1 | 8/2005 | Oshlack et al. |
| 2005/0245483 A1 | 11/2005 | Brogmann et al. |
| 2005/0245556 A1 | 11/2005 | Brogmann et al. |
| 2005/0272776 A1 | 12/2005 | Buehler |
| 2006/0039970 A1 | 2/2006 | Oshlack et al. |
| 2006/0182801 A1 | 8/2006 | Breder et al. |
| 2007/0122348 A1 | 5/2007 | Kaiko et al. |
| 2007/0185146 A1 | 8/2007 | Fleischer et al. |
| 2008/0145429 A1 | 6/2008 | Leyendecker et al. |

FOREIGN PATENT DOCUMENTS

| | | |
|---|---|---|
| CA | 2478515 | 10/2003 |
| CA | 2478523 | 10/2003 |
| CA | 2372025 | 9/2007 |
| DE | 2138593 | 3/1972 |
| DE | 2222039 | 11/1972 |
| DE | 4325465 | 2/1995 |
| DE | 29719704 | 1/1998 |
| DE | 19651551 | 6/1998 |
| DE | 19857766 | 12/1999 |
| DE | 19859636 | 6/2000 |
| DE | 19918325 | 10/2000 |
| DE | 19938823 | 2/2001 |
| EP | 0193355 | 9/1986 |
| EP | 0205282 | 12/1986 |
| EP | 0319243 | 6/1989 |
| EP | 0352361 | 1/1990 |
| EP | 0527638 | 2/1993 |
| EP | 0576643 | 6/1993 |
| EP | 624366 | 11/1994 |
| EP | 0631781 | 1/1995 |
| EP | 0647448 | 4/1995 |
| EP | 0699436 | 3/1996 |
| EP | 0880352 | 2/1998 |
| EP | 0913152 | 5/1999 |
| EP | 1201233 | 5/2002 |
| EP | 1348429 | 10/2003 |
| EP | 1364649 | 11/2003 |
| EP | 1604666 | 12/2005 |
| EP | 1041987 B1 | 4/2006 |
| EP | 1695700 | 8/2006 |
| EP | 1813276 | 8/2007 |
| GB | 1353815 | 5/1974 |
| GB | 1390772 | 4/1975 |
| JP | H10-251149 | 9/1998 |
| NZ | 260408 | 5/1996 |
| NZ | 264953 | 11/1996 |
| NZ | 260883 | 6/1997 |
| NZ | 294897 | 10/1998 |
| NZ | 544181 | 12/2008 |
| RU | 98102450 | 7/1996 |
| RU | 2222260 | 1/2004 |
| WO | WO 1983/03197 | 9/1983 |
| WO | WO 1987/01282 | 3/1987 |
| WO | WO 1990/04965 | 5/1990 |
| WO | WO 1993/010765 | 6/1993 |
| WO | WO 1994/06426 | 3/1994 |
| WO | WO 1995/03804 | 2/1995 |
| WO | WO 1996/02251 | 2/1996 |
| WO | WO 1996/014058 | 5/1996 |
| WO | WO 1996/014059 | 5/1996 |
| WO | WO 1997/33566 | 9/1997 |
| WO | WO 1997/45091 | 12/1997 |
| WO | WO 1998/025613 | 6/1998 |
| WO | WO 1998/35679 | 8/1998 |
| WO | WO 1999/001111 | 1/1999 |
| WO | WO 1999/005960 | 2/1999 |
| WO | WO 1999-11250 | 3/1999 |
| WO | WO 1999/022737 | 5/1999 |
| WO | WO 1999/32119 | 7/1999 |
| WO | WO 1999/32120 | 7/1999 |
| WO | WO 2000/01377 | 1/2000 |
| WO | WO 2000/025821 | 5/2000 |
| WO | WO 2000/38649 | 7/2000 |
| WO | WO 2000/41683 | 7/2000 |
| WO | WO 2000/051592 | 9/2000 |
| WO | WO 2000/067739 | 11/2000 |
| WO | WO 2001/032180 | 5/2001 |
| WO | WO 2001/37785 | 5/2001 |
| WO | WO 2001/52851 | 7/2001 |
| WO | WO 2001/58447 | 8/2001 |
| WO | WO 2001/58451 | 8/2001 |
| WO | WO 2001-158447 | 8/2001 |
| WO | WO 2001/68080 | 9/2001 |
| WO | WO 2001/85150 | 11/2001 |
| WO | WO 2001/85257 | 11/2001 |
| WO | WO 2001/93852 | 12/2001 |
| WO | WO 2002/087512 | 11/2002 |
| WO | WO 2002/092059 | 11/2002 |
| WO | WO 2002/092060 | 11/2002 |
| WO | WO 2003/003541 | 1/2003 |
| WO | WO 2003/004009 | 1/2003 |
| WO | WO 2003/007802 | 1/2003 |
| WO | WO 2003/013476 | 2/2003 |

(56) References Cited

FOREIGN PATENT DOCUMENTS

| | | |
|---|---|---|
| WO | WO 2003/013479 | 2/2003 |
| WO | WO 2003/013538 | 2/2003 |
| WO | WO 2003/020124 | 3/2003 |
| WO | WO 2003/024429 | 3/2003 |
| WO | WO 2003/024430 | 3/2003 |
| WO | WO 2003/026676 | 4/2003 |
| WO | WO 2003/073937 | 9/2003 |
| WO | WO 2003/084504 | 10/2003 |
| WO | WO 2003/084520 | 10/2003 |
| WO | WO 2004/026262 | 4/2004 |
| WO | WO 2004/064807 | 8/2004 |
| WO | WO 2004/091623 | 10/2004 |
| WO | WO 2005/000310 | 1/2005 |
| WO | WO 2005/025621 | 3/2005 |
| WO | WO 2005/079760 | 9/2005 |
| WO | WO 2005/120506 | 12/2005 |
| WO | WO 2005/120507 | 12/2005 |
| WO | WO 2006/024881 | 3/2006 |
| WO | WO 2006/079550 | 8/2006 |
| WO | WO 2006/089970 | 8/2006 |
| WO | WO 2006/089973 | 8/2006 |
| WO | WO 2007/047935 | 4/2007 |
| WO | WO 2007/085637 | 8/2007 |
| WO | WO 2007/088489 | 8/2007 |
| WO | WO 2007/111945 | 10/2007 |
| WO | WO 2007/123865 | 11/2007 |
| WO | WO 2008/025790 | 3/2008 |
| WO | WO 2008/030567 | 3/2008 |
| WO | WO 2009/040394 | 4/2009 |
| WO | WO 2010/003963 | 1/2010 |
| WO | WO 2010/103039 | 9/2010 |
| WO | WO 2012/020097 | 2/2012 |

OTHER PUBLICATIONS

Abernethy et al., Randomised, double blind, placebo controlled crossover trial of sustained release morphine for the management of refractory dyspnoea, BMJ, vol. 327, 6 pages (2003).
Alvarez-Fuentes et al. "Effectiveness of Repeated Administration of a New Oral Naltrexone Controlled-Release System in Morphine Analgesia"; J. Pharm Pharmacol (2001), 53:1201-1205.
Alvarez-Fuentes, et al., "Preclinical Study of an Oral Controlled Release Naltrexone Complex in Mice"; J. Pharm Pharmacol (2000), 52:659-663.
Amass et al., "Efficacy of daily and alternate-day dosing regimens with the combibation buprenorphine-naloxone tablet"; Drug and Alcohol Dependence (2000) vol. 58, pp. 143-152.
Amati et al., "In vitro effects of naloxone on T-lymphocyte-dependent antibacterial activity in hepatitis C virus (HCV) infected patients and in inflammatory bowel disease (IBD) patient," lmmunopharmacology and lmmonotoxicology, vol. 23, No. 1 (2001), pp. 1-11 (2001).
Archer Sydney; "Historical Perspective on the Chemistry and Development of Naltrexone"; Naltrexone Research Monograph28 (1980) p. 3-9.
Azamari et al., "Thermal treating as a tool for sustained release of indomethacin from Eudragit RS and RL matrices," International Journal of Pharmaceutics, 246, 171-177 (2002).
Barton et al., "Intranasal Administration of Naloxone by Paramedics";Prehospital Emergency Care (2002) vol. 6, No. 1, pp. 54-58.
Bashaw et al., "Relative bioavailability of controlled-release oral morphine sulfate during naltrexone blockade"; Inter J of Clin Pharm and Thea (1995) vol. 33, No. 9, 524-529.
Baum et al., "The Impact of the Addition of Naloxone on the Use and Abuse of Pentazocine"; Public Health Reports (1987) vol. 102, No. 4 p. 426-429.
Beauford et al., "Effects of Nebulized Morphine Sulfate on the Exercise Tolerance Ventilatory Limited COPD Patient," Chest, vol. 104, No. 1, pp. 175-178 (1993).

Benfey "Function of Myocardial-Adrenoceptors" ; Life Sciences (1982) vol. 31, pp. 101-112.
Benziger et al., "Differential effects of food on the bioavailability of controlled release oxycodone tablets and it oxycodone solution" J Pharm Sciences, vol. 85, No. 4, pp. 407-410 (1996).
Berkow, R. (ed.) Merck Manual of Medical Information, pp. 528-530 (1997).
Berkow, R. (ed.) The Merck Manual of Diagnosis and Therapy (1997), extract (English Translation from Russian).
Bigelow et al., "Abuse Liability and Assessment of Buprenorphine-Naloxone Combinations"; Dept of Psychiatry and Behavioral Sciences, The Johns Hopkins University School of Medicine, pp. 145-149, (1987).
Blachly Paul, H., M.D., "Naloxone in Opiate Addiction"; Current Psychiatric Therapies (1976) pp. 209-213.
Bloom et al., "Clinical Studies with Naloxone/Methadone in a Ratio of 1:20"; 5th National Conference on Methadone Treatment (1973) vol. 2, p. 1342-1349.
Brennscheidt et al., "Pharmacokinetics of Nortilidine and Naloxone after Administration of Tilidine/Naloxone Solution or Tilidine/Naloxone Sustained Release Tablets"; Arzeim-Forsch/Drug Res. (2000) vol. 50, pp. 1015-1022.
Briscoe et al., "Methoclocinnamox: Time Course of Changes in Alfetnanil-Reinforced Rhesus Monkeys"; Psychopharmacology (2000) 148:393-399.
Bromm et al., "A Sensitive Method to Evaluate Effects of Analgesics in Man"; Meth and Find Exptl Clin Pharmacol 5 (8) (1983) p. 545-551 (abstract).
Budd, Keith, "Clinical Use of Opioid Antagonists"; Bailliere's Clinical Anesthesiology (1987) vol. 1, No. 4, pp. 993-1011.
Bullingham et al., "Clinical Pharmacokinetics of Narcotic Agonist-Antagonist Drugs"; Clinical Pharm (1983) 8: 332-343.
Bunzow et al., "Molecular cloning and tissue distribution of a putative member of the rat opioid receptor gene family that is not a mu, delta or kappa opioid receptor type." FEBS Lett. Jun. 27, 1994;347(2-3):284-8.
Caldwell et al., "Treatment of Osteoarthritis Pain with Controlled Release Oxycodone or Fixed Combination Oxycodone Plus Acetaminophen Added to Nonsteroidal Antiinflammatoiy Drugs: A Double Blind, Randomized, Multicenter, Placebo Controlled Trial," J Rheumatol. vol. 26, No. 4, pp. 862-869 (1999).
Calimlim, et al. "Effect of Naloxone on the Analgesic Activity of Methadone in a 1:10 Oral Combination"; Clin Pharmacol and There (1974) vol. 15; No. 6 pp. 556-564.
Cappel et al., "Enhancement of Naloxone Induced Analgesia by Pretreatment with Morphine" Pharma. Bioch. & Behav. (1989), 34:425-427.
Caruso et al., "Methadone and Naloxone in Combination (Naldone®) for the Treatment of Heroin Addicts"; Bristol Laboratories, pp. 1336-1341 (1973).
Chambers Dictionary of Science and Technology, Ed. P.M.B. Walker, Chambers, 1999, p. 803.
Chen et al., "Challenges and New Technologies of Oral Controlled Release," Oral Controlled Release Formulation Design and Drug Delivery: Theory to Practice (2010) pp. 257-277.
Chen et al., "Oral naloxone reverses opioid-associated constipation," Foreign Medical Sciences: Anesthesiology and Resuscitation, vol. 21, No. 5, p. 319 (2000).
Cherny Nathan I., "Opioid Analgesics"; Drugs May 1996:51 (5) pp. 713-737.
Cherry et al., "Opioids in Pain Therapy," The Frankfurt Consensus, STK—Special Issue 2001 Article 2 (3 pages) (in German, w/ English translation).
Chiang et al. "Clinical Evaluation of a Naltrexone Sustained-Release Preparation"; Drug and Alcohol Dependence (1985) 16, pp. 1-8.
Chiang et al., "Kinetics of a Naltrexone Sustained-Release Preparation"; Clin Pharmacy Thera (1984) vol. 36 No. 5, pp. 704-708.
Chien, Chih-Cheng et al., "Sigma Antagonists Potentiate Opioid Analgesia in Rats", Neuroscience Letters 190 (1995), 137-139.
Choi et al., "Opioid Antagonists: A Review of Their Role in Palliative care, Focusing on Use in Opioid-Related Constipation," J. of Pain and Symptom Management, vol. 24(1): 71-90.

(56) References Cited

OTHER PUBLICATIONS

Ciccocioppo et al., "Effect of Nociceptin/orphanin FQ on the Rewarding Properties of Morphine"; Eur. J Pharmacol (2000) vol. 404, pp. 153-159.
Citron et al., "Long-term administration of controlled release oxycodone tablets for the treatment of cancer pain," Cancer Investigation, vol. 16, No. 8, pp. 562-571 (1998).
Clark et al., "Symptom indexes to assess outcomes of treatment for early prostate cancer" Medical Care (2001) 39(10) 1118-1130.
Clemens et al., "Combined oral prolonged-release oxycodone and naloxone in opioid-induced bowel dysfunction: review of efficacy and safety data in the treatment of patients experiencing chronic pain," Expert Opinion on Pharmacotherapy, 11(2):297-310 (2010).
Cohen Statistical Power Analysis for the Behavioral Sciences (2nd ed.) Hillsdale, NJ: Erlbaum (1988).
Comer et al., "Depot Naltrexone: Long-lasting Antagonism of the Effects of Heroin un Humans"; Psychopharmacology (2002) 159, pp. 351-360.
Complaint for Declaratory Judgment filed in the United States District Court for the Western District Court of Virginia on Nov. 17, 2008, Civil Action No. 1:08CV00050.
Crabtree et al., "Review of Naltrexone, a long-acting Opiate Antagonist"; Clinical Pharmacy, vol. 3 (1984) pp. 273-280.
Crain et al. "Antagonists of excitatory opioid receptor functions enhance morphine's analgesic potency and attenuate opioid tolerance/dependence liability," Pain, vol. 84 pp. 121-131 (2000).
Crain et al., "Acute thermal hyperalgesia elicited by low-dose morphine in normal mice is blocked by ultra-low-dose naltrexone, unmasking potent opioid analgesia"; Brain Research (2001) vol. 888, pp. 75-82.
Crain et al., "Antagonists of Excitatory Opioid Receptor Functions Enhance Morphine's Analgesic Potency and Attenuate Opioid Tolerance/dependence liability"; Dept. of Neuroscience, Albert Einstein College of Medicine Pain 84 (2000) pp. 121-131.
Crain et al., "Ultra-Low Concentrations of Naloxone Selectively Antagonize Excitory Effects of Morphine on Sensory Neurons, Thereby Increasing Its Antinociceptive Potency and Attenuating Tolerance/Dependence During Chronic Cotreatment," Proc. Natl. Acad. Sci. USA (1995) 92:10540-10544.
Culpepper-Morgan et al., "Treatment of opioid-induced constipation with oral naloxone: A pilot study." Clinical Trials and Therapeutics, (1992) vol. 52(1): 90-95.
Davies, S., "Rising to the pain challenge," Drug News Perspect, 19(10):653-8 (2006).
Delbarre et al., Naloxone effects on blood pressure, analgesia and dieresis in spontaneous hypertensive and normotensive rats; Neuroscience Letters, vol. 30; pp. 167-172 (1982).
Deyo et al. "Reproducibility and responsiveness of health status measures. Statistics and strategies for evaluation" Cont. Clin. Trials (1991) 12:142S-158S.
Di Giannuario et al., "Orphanin FQ reduces morphine-induced dopamine release in the nucleus accumbens: a microdialysis study in rats"; Neurosci. Lett (1999) vol. 272 pp. 183-186.
Dictionary of Modern Computer Terms, S.-P.: BHV-Petersburg, p. 215 (2004).
Drossman et al. "Rome II: The Functional Gastrointestinal Disorders," 2nd ed. (2000) McLean, VA: Degon Associates.
Ebell et al., "The management of pain in cancer patients," Supportive Measures in Oncology, Jehn et al., eds., 1994, vol. 3 (in German, w/ English translation).
Eissenberg et al. "Buprenophine's physical dependence potential: Antagonist-precipitated withdrawal in humans," J. Pharmacol. Exp. Therapeut. vol. 276, No. 2, p. 449 (1996).
EP Application No. EP05020579.8: Communication forwarding the European Search Report dated Feb. 7, 2006.
EP Application No. EP05020580.6: Communication forwarding the European Search Report dated Feb. 8, 2006.
EP Application No. EP06111805.5: Jul. 10, 2008 Response to Office Communication dated Feb. 19, 2008.
EP Application No. EP10176078.3: Communication forwarding the European Search Report dated Mar. 8, 2011.
EP Application No. EP10180364.1: Office Communication and European Search Report, dated Dec. 10, 2010.
EP Application No. EP10180425.0: Office Communication and European Search Report, dated Dec. 10, 2010.
EP Application No. EP10180494.6: Communication forwarding the European Search Report dated Mar. 9, 2011.
EP Application No. EP10180495.3: Communication forwarding the European Search Report dated Feb. 25, 2011.
EP Application No. EP10180496.1: Communication forwarding the European Search Report dated Mar. 9, 2011.
EP Application No. EP10180498.7: Communication forwarding the European Search Report dated Mar. 9, 2011.
EP Application No. EP11177513.6: European Search report and Search opinion dated Feb. 2, 2012.
EP Application No. EP11177516.9: European Search report and Search opinion dated Feb. 2, 2012.
EP Application No. EP11177518.5: European Search report and Search opinion dated Feb. 2, 2012.
EP Application No. EP11177520.1: European Search report and Search opinion dated Feb. 2, 2012.
European Patent No. EP1492506: Hexal Opposition (English Translation only) dated Sep. 30, 2009 (12 pages).
Excerpt from Industrial Pharmacy, "Classification of drug delivery systems," 1996 (English translation).
Fink et al., "Naloxone in Heroin Dependence"; Clin Pharm and Thera. vol. 9, No. 5;pp. 568-577, (1968).
Fishman et al., "Disposition of Naloxone-7,8-3H in Normal & Narcotic Dependent Men"; J. Pharm. and Exper. Thera (1973)vol. 10 No. 2;pp. 575-580.
Forth et al., General and Special Pharmacology and Toxicology, 7th rev. ed., 1996, pp. 207-217 (in German w/English Translation).
Foss et al., "Dose related Antagonism of the Emetic Effect of Morphine by Methylnaltrexone in Dogs",J. Clin Pharmacol (1993), 33:747-751.
Foss J.F., et al. Abstract, "Prevention of Apomorphine- or Cisplatin-induced emesis in the dog by combination of Methylnaltrexone and Morphine",Cancer Chemother Pharmacol (1998); 42(4):287-91.
Fraser Albert D., et al., "Clinical Toxicology of Drugs Used in the Treatment of Opiate Dependency"; Clinical Toxicology I (1990) vol. 10, No. 2; pp. 375-386.
Freye et al., 'Effects of Tramadol and Tilidine/Naloxone on Oral-Caecal Transit & Pupillary light Reflex'; Arzneim-Forsch/Drug Res. 50(I)(2000)pp. 24-30.
Fudala et al., "Effects of Buprenorphine and Naloxone in Morphine-Stabilized Opioid Addicts"; Drug and Alcohol Dependence 50 (1998) pp. 1-8.
Fudala et al., "Human Pharmacology and Abuse Potential of Nalmefene"; Clin Pharm and Thera (1991) vol. 49, 3, pp. 300-306.
Gal et al., "Prolonged Blockade of Opioid Effect with Oral Nalmefene"; Clin Pharm and Thera (1986) pp. 537-542.
Gan et al., "Opioid-Sparing Effects of a Low-Dose Infusion of Naloxone in Patient-Administered Morphine Sulfate," Anesthesiology (1997), 87(5):1075-1080.
Gerra et al., "Clonidine and Opiate Receptor Antagonists in the Treatment of Heroin Addiction"; J. Substance Abuse Treatment (1995) vol. 12, 1, pp. 35-41.
Ghodse et al., "Opioid analgesics and Narcotic Antagonists"; Side Effects of Drugs (2000) Annual 23, chpt 8 pp. 96-113.
Glatt William, M.D. FACP, "A New Method for Detoxifying Opioid-Dependent Patients"; J. Substance Abuse Treatment (1999) vol. 17, No. 3,pp. 193-197.
Gold et al. "Rapid Opioid Detoxification During General Anesthesia"; Anesthesiology (1999) vol. 91, No. 6, pp. 1639-1647.
Goliber (Benchtop Evaluations of Tampering with Pharmaceutical Dosage Forms, Opioid Abuse Resistance Conference, Oct. 2005—Accessed from http://www.thci.org/opioid/oct05docs/TAB%205.8%20Gober.%20Benchtop%20Evaluations%20of%20Tampering%20with%20Pharmaceutical%20Disage%20Forms.pdf on Nov. 17, 2010.

(56) References Cited

OTHER PUBLICATIONS

Gonzalez et al., "Naltrexone: A Review of its Pharmacodynamic and Pharmacokinetic Properties and Therapeutic Efficacy in the Management of Opioid Dependence," Drugs (1988), 35:192-213.
Goodman and Gilman's The Pharmacological Basis of Therapeutics (Tenth Edition (2001), McGraw Hill.
Goodridge et al., "Factors associated with opioid dispensation for patients with COPD and lung cancer in the last year of life: A retrospective analysis," Int. J. of COPD, 2010, 5:99-105.
Greenwald et al., "Comparative Clinical Pharmacology of Short-Acting Opioids in Drug Abusers"; J. Pharm and Exper Thera (1996) vol. 277, No. 3, pp. 1228-1236.
Grimm, "Extension of the International Conference on Harmonization Tripartite Guideline for Stability Testing of New Drug Substances and Products to Countries of Climatic Zones III and IV," Drug Development and Industrial Pharmacy, vol. 24, No. 4, pp. 312-324 (1998).
Gupta et al., "Morphine Combined with Doxapram or Naloxone"; Anesthesia (1974) vol. 29, pp. 33-39.
Guyatt et al. "Measuring change over time: assessing the usefulness of evaluative instruments" J. Chron Dis. (1987) 40(2):171-178.
Guyatt et al., "Interpreting treatment effects in randomized trials," Br. Med. Jnl, (1998) 316(7132): 690-693.
Hagen, et al. "Efficacy, Safety, and Steady-State Pharmacokinetics of Once-A-Day Controlled-Release Morphine (MS Contin XL) in Cancer Pain," Journal of Pain and Symptom Management (2005) vol. 29, No. 1, pp. 80-90.
Han et al., "Muccoadhesive buccal disks for novel nalbuphine prodrug controlled delivery; effect of formulation variable on drug release and mucoadhesive performance"; International J. Pharm (1999) vol. 177, pp. 201-209.
Handal et al., "Naloxone"; Annals of Emergency Medicine (1983) vol. 12:7, pp. 438-445.
Hanson Analgesic, Antipyretic and Anti-Inflammatory Drugs in Remington's Science and Practice of Pharmacy (1995), 2:1207.
Harris et al., "Buprenorphine and Naloxone co-administration in opiate dependent patients stabilized on sublingual buprenorphine"; Drug and Alcohol Dependence (2000) vol. 61, pp. 85-94.
Hawkes et al., "Effect of enteric-release formulation of naloxone on intestinal transit in volunteers taking codeine"; Aliment Pharm Ther (2001) vol. 15, pp. 625-630.
Hays et al. "Assessing reliability and validity of measurement in clinical trials" in Staquet et al. (eds.) Quality of Life in Clinical Trials: Methods and Practice (1998) Oxford: Oxford University Press.
Hening et al., "Dyskinesias while awake and periodic movements in sleep in restless legs syndrome: Treatment with opioids," Neurology, vol. 36, pp. 1363-1366 (1986).
Hiroshi K., et al., "Pharmacology," Hirokawa Bookstore, 1992, p. 70-72.
Hogger et al., "Comparison of tilidine/naloxone, tramadol and bromfenac in experimental pain: a double-blind randomized crossover study in healthy human volunteers"; International J. Clin Pharm and Thera (1999) vol. 37, No. 8,pp. 377-385.
Holmes et al., "Inhibiting Spinal Dynorphin A Component Enhances Intrathecal Morphine Antinociception in Mice", Anesth. Analg. (1993), 77:1166-73.
Holzer et al., "Opioid-induced bowel dysfunction in cancer-related pain: causes, consequences and a novel approach for its management," Journal of Opioid Management, 5(3): 145-151 (2009).
Hopp et al., "Analgesic efficacy of oxycodone in combination with naloxone as prolonged release (PR) tablets in patients with moderate to severe chronic pain [abstract PT 226]," Presented at the 12th World Congress on Pain, International Association for the Study of Pain (IASP), Glasgow, Scotland, UK, MIS 4789879, Aug. 17-22, 2008.
Hopp et al., "Pain 2: Oral prolonged-release (PR) oxycodone/naloxone combination reduces opiod-induced bowel dysfunction (OIBD) in chronic pain patients [abstract 40]," Presented at the 5th Research Forum of the European Association for Palliative Care, Palliat. Med., 22(4):441 (2008).
Howes et al., "The Pharmacology of TR5109, a new Narcotic Agonist/Antagonist Analgesic"; NIDA Research (1979) pp. 99-105.
Hughes et al., "Buprenorphine for pain relief in a patient with drug abuse," The American Journal of Drug and Alcohol Abuse, vol. 17, No. 4, pp. 451-455 (1991).
Hussain et al., "Buccal and oral bioavailability of naloxone and naltrexone in rats";(1987) vol. 36, pp. 127-130.
Hussain M.A. "Improved buccal delivery of opioid analgesics and antagonists with bitterless prodrugs." Pharm. Res. 1988, 5(9):615-618.
Inoue, "On the Treatment of Restless Legs Syndrome," Progress in RLS Research, vol. 24, No. 3, pp. 892-897 (2004).
Israel Patent Appln. No. 192973: office Action dated Sep. 14, 2010, with report letter dated Oct. 24, 2010 as translation (8 pages).
Jasinski D.R., "Assessment of the Abuse Potentiality of Morphine-like Drugs (Methods Used in Man)"; Drug Addiction (1977) pp. 197-258.
Jasinski et al., "The human pharmacology and abuse potential of N-allylnoroxymorphone naloxone"; J. Pharm and Exper Thera (1967) vol. 157, No. 2, pp. 420-426.
Johnson et al., "Buprenorphine and Naloxone for Heroin Dependence"; Substance Use Disorders (2000) pp. 519-526.
Jones et al., "Nalmefene:blockade of intravenous morphine challenge effects in opioid abuse in humans"; Drug and Alcohol Dependence (2000) vol. 60, pp. 29-37.
Judson et al., "The Naloxone Test for Opiate Dependence," Clin. Pharmacol. Ther., vol. 27, No. 4, pp. 492-501, (1980).
Kanof et al., "Clinical characteristics of naloxone-precipitated withdrawal in human opioid-dependent subjects," J. Pharmacol. Exp. Therapeut., vol. 260, No. 1, pp. 355-363 (1992).
Kanof et al., "Levels of Opioid Physical Dependence in Heroin Addicts," Drug and Alcohol Dependence, 27 (1991) 253-262.
Kapoor, S., "Emerging New Therapeutic Options for the Management of Opioid Induced Constipation," J. of Pain and Palliative Case Pharmacotherapy, 24(1):98-99 (2010).
Kazis et al. "Effects sizes for interpreting changes in health status," Med. Care 27(3 Suppl.):S178-S189 (1989).
King et al., "Naltrexone Biotransformation and Incidence of Subjective Side Effects: A Preliminary Study"; Alcoholism: Clin and Exper Res (1997) vol. 21, No. 5, pp. 906-909.
Kogan et al., "Estimation of the Systemic Availability and Other Pharmacokinetic Parameters of Naltrexone in Man after Acute and Chronic Oral Administration"; Res. Comm. In Chem. Path. and Pharm (1977) vol. 18, No. 1, pp. 29-34.
Kosten et al., "Opioid antagonist challenges in buprenorphine maintained patients"; Drug and Alcohol Dependence (1990) vol. 25, OO. 73-78.
Kosten Thomas R., M.D.,"Buprenorphine for Benzodiazepine-Abusing Heroin Addicts"; Amer J of Psychiatry (1994) vol. 1, p. 151.
Kreek et al., "Drug Interactions with Methadone," *Ann. N.Y. Acad. Sci.*, 281, 350-371 (1976).
Krylov, Drug Register of Russia, Encyclopedia of Drugs, (2001) entries for "Nalbuphine," "Naloxone," and "Naltrexone" (English Translation).
Kurland et al., "Naloxone and the Narcotic Abuser: A Cont oiled Study of Partial Blockade"; Inter. J. of the Addictions (1974) vol. 9, No. 5, pp. 663-672.
Kurz et al., "Opioid-Induced Bowel Dysfunction: Pathophysiology and Potential New Therapies," Drugs, vol. 63, No. 7, pp. 649-671 (2003), abstract.
Lamprecht et al., "Biodegradable microparticles as a two-drug controlled release formulation: a potential treatment of inflammatory bowel disease"; Journal of Controlled Release, vol. 69, pp. 445-454 (2000).
Lapierre "Acetaminophen Boosts Liver Toxicity Alone, as Combination Therapy-Jama" Health News Daily, vol. 18 Issue 128 dated Jul. 6, 2006.

(56) References Cited

OTHER PUBLICATIONS

Latasch et al., "Aufhebun einer Morphin-induzierten Obstipation durch orales Naloxon," with translation ("Oral Naloxone Antagonizes Morphine-Induced Constipation"), Anaesthesist, 46, 191-194 (1997).
Lee et al., "Nalbuphine Coadministered with Morphine Prevents Tolerance and Dependence"; Anesth Analg (1997) vol. 84, pp. 810-815.
Leehey et al., Naloxone increases water and electrolyte excretion after water loading in patients with cirrhosis and ascites, J of lab and clin med; vol. 118, No. 5, pp. 484-491 (1991).
Leeling et al., "Disposition and metabolism of codorphone in the rat, dog, and man"; Drug Metabolism and Disposition (1982) vol. 10, No. 6, pp. 649-653.
Lehman et al., "Influence of Naloxone on the Postoperative Analgesic and Respiratory effects of Buprenorphine"; Eur. J. Clin Pharm (1988) vol. 34, pp. 343-352.
Leidy et al., "Recommendations for evaluating the validity of quality of life claims for labeling and promotion," Value in Health 2(2): 113-127 (1999).
Levine et al., "Potentiation of Pentazocine Analgesia by Low-dose Naloxone"; J Clin Invest (1988) vol. 82, pp. 1574-1577.
Levy M.H., Eur J Pain.vol. 5, Suppl. A, pp. 113-116 (2001), abstract.
Light et al., "Effects of Oral Morphine in Breathlessness and Exercise tolerance in Patients with Chronic Obstructive Pulmonary Disease," Am. Rev. Respir. Dis., (1989) vol. 139, pp. 126.
Liu et al., "Low dose oral naloxone reverses opioid-induced constipation and analgesia"; Journal of Pain and Symptom Management, vol. 23, No. 1, pp. 48-53 (2002).
Loimer et al., "Combined Naloxone/Methadone Preparations for Opiate Substitution Therapy"; J. of Substance Abuse Treatment (1991) vol. 8, pp. 157-160.
Lorcet, Physicians' Desk Reference 48th ed., 1994; pp. 2388-2390.
Lortab, Physicians' Desk Reference 48th ed., 1994; pp. 2498-2500.
Lowenstein et al., "Combined prolonged release oxycodone and naloxone improves bowel function in patients receiving opioids for moderate-to-severe non-malignant chronic pain: a randomized controlled trial," Expert Opinion on Pharmacotherapy, 10(4):531-543 (2009).
Martin et al. "Bioavailability Investigation of a New Tilidine/Naloxone Liquid Formulation Compared to a Reference Formulation";Arzneim-Forsch./Drug Res. (1999) vol. 49, pp. 599-607.
Martin et al., "Demonstration of Tolerance to and Physical Dependence on N-allynormorphine (Nalorphine)";J. of Pharm and Exper Thera (1965) vol. 150, No. 3. pp. 437-442.
Medzon, R, "Naltrexone and Nalmefene," Clinical Toxicology Review, vol. 19, No. 3, Dec. 1996.
Meissner et al., "A randomized controlled trial with prolonged-release oral oxycodone and naloxone to prevent and reverse opioid-induced constipation," Eur. J. Pain, vol. 13, pp. 56-64 (2009).
Meissner et al., "Oral naloxone reverses opioid-associated constipation", Pain, vol. 84, pp. 105-109 (2000).
Mendelson et al., "Buprenophine and naloxone Interactions in Methadone Maintenance Patients"; Society of Biological Psychiatry (1997) vol. 41, pp. 1095-1101.
Mendelson et al., "Buprenorphine and naloxone combinations: the effects of three dose ratios in morphine stabilized, opiate-dependent volunteers"; Psychopharmacology (1999) vol. 141, pp. 37-46.
Mendelson J., et al, "Buprenorphine and Naloxone Interactions in Opiate Dependent Volunteers," Clin. Phar. Ther. (1996), 60:105-114.
Miaskowski et al., "Inhibition of Spinal Opioid Analgesia by Supraspinal Administration of Selective Opioid Antagonists", Brain Research (1992), 596:41-45).
Mikus, G., "Combining Opioid Agonists and Antagonists as a Solution for Opioid-induced Constipation," European Gastroenterology and Hepatology Review, 4(2):71-74 (2008).
Mims, Jan. 2005, pp. 120-125.

Mollereau et al., "ORL 1, a novel member of the opioid receptor family: Cloning, functional expression and localization"; FEBS letters 341 (1994), pp. 33-38.
Mueller-Lissner, "Fixed Combination of Oxycodone with Naloxone: a New Way to Prevent and Treat Opioid-Induced Constipation." Adv. Ther. (2010) 27(9):581-590.
Muller-Lissner et al., "Oral Prolonged release (PR) oxycodone/naloxone combination reduced opioid-induced bowel dysfunction (OIBD) in patients with severe chronic pain (abstract 189)," Presented at the 2nd International Congress on Neuropathic Pain, Berlin, Germany, Published in Eur. J. Pain, 11(S1): S82, Jun. 7-10, 2007.
Mundipharma Clinical Studies Report A2-3759, "Validation of Bowel Function Index," Jun. 15, 2005 (Rev. Jul. 12, 2005).
Mundipharma Clinical Studies Report OXN 2401, "Optimization of Naloxone-Oxycodone Ration in Pain Patients." Jun. 3, 2005.
Mundipharma Clinical Study Results for Controlled Release of Oxycodone/Naloxone Formulations, Phase II Study (undated).
Mundipharma's Opposition to Endo's Australian Patent Application No. AU2002305559, filed Oct. 1, 2008.
Nadstawek et al., "Patient assessment of a novel therapeutic approach for the treatment of severe, chronic pain," Int. J. Clin. Pract., vol. 62, No. 8, pp. 1159-1167 (2008).
Nadstawek et al., "Patient assessment of the efficacy and tolerability of coadministered prolonged release oral oxycodone and naloxone in severe chronic pain (abstract SAT0375)," Presented at the 8th Annual European League Against Rheumatism (EULAR 2007), Barcelona, Spain, Published in Ann. Rheum. Dis., 66(Suppl. 2):543, Jun. 13-16, 2007.
Neuenschwander et al., Palliative Medicine at a Glance, 1999 (whole book).
Nichols et al., "Improved bowel function with a combination of oxycodone and naloxone (OXN) as prolonged-release (PR) tablets in patients with moderate to severe chronic pain (abstract PT225)," Presented at the 12th World Congress on Pain, International Association for the Study of Pain (IASP), Glasgow, Scotland, UK, Aug. 17-22, 2008.
Nolte, T., "Prolonged-release oxycodone/naloxone is effective and safe in clinical use (abstract 275)," Encore presentation at the 5th Research Forum of the European Association for Palliative Care, Published in Palliative Medicine, 22(4):484-5 (2008).
Nolte, T., "Prolonged-release oxycodone/naloxone is effective and safe in cancer pain (abstract 66)," Encore presentation at the 12th World Congress on Pain, International Association for the Study of Pain (IASP), Glasgow, Scotland, UK, Aug. 17-22, 2008.
Nolte, T., "Prolonged-release oxycodone/naloxone is effective and safe in clinical use (abstract PO325)," Presented at the 28th German Congress on Cancer, Published in Onkologie, Berlin, Germany, 31(Suppl. 1):165-6, Feb. 20-23, 2008.
Norman et al., "Interpretation of changes in health-related quality of life: The remarkable universality of half a standard deviation." Med. Care 41:582-592 (2003).
Nunnally et al. Psychometric Theory (3rd Edition) NY: McGraw-Hill (1994).
Nutt et al., "Methadone-naloxone mixture for use in methadone maintenance programs"; Clin Pharm and Ther. vol. 15, No. 2., pp. 156-166 (1974).
Oppermann M., "Nene Arzneimittel zur Behandlung der Opioid-induzierten und Obstipation: der Mechanismus-basierte Ansatz von Methylnaltrexon, Naloxon and Alvimopan," Fortbildungstelegramm Pharmazie; May 1, 2009; pp. 117-131.
Oxygesic® Product Information, 1997-2001 (in German, w/ English translation).
Package Insert for OxyContin®, Purdue Pharma L.P. (Mar. 18, 2004).
Paille et al., "An open six-month study of the safety of Transipeg for treating constipation in community medicine," J. Clin. Res., vol. 2, pp. 65-76 (1999).
Pamuk et al., "Revalidation of description of constipation in terms of recall bias and visual scale analog questionnaire," Journal of Gastroenterology Hepatology (2003), 18, 1417-1422.
Pappagallo, M., "Incidence, prevalence, and management of opioid bowel dysfunction," Am. J. Surg. (2001) 182 suppl. 11S-18S.

(56) References Cited

OTHER PUBLICATIONS

Paronis et al., "Increased Analgesic Potency of Mu Agonists after Continuous Naloxone Infusion in Rats"; J for Pharm Exper Thera (1991), 259 (2), pp. 582-589.
Parwartikar et al., "Naloxone-Methadone Combination for the Treatment of Opiate Dependence"; Missouri Institute of Psychiatry, pp. 1350-1354, (1973).
Parwatikar et al., "Methadone-naloxone in combination for the Treatment of Heroin Addicts"; Clin. Pharm and Thera, vol. 14, No. 6, pp. 941-948, (1973).
PCT Application PCT/EP2003/003541: International Preliminary Examination Report dated Jul. 6, 2004.
PCT Application PCT/EP2005/006155: International Search Report dated Aug. 25, 2005 (2 pages).
PCT/EP2009/058630: Notification of Transmittal of the International Search Report and the Written Opinion of the International Searching Authority, or the Declaration (with International Search Report, and Written Opinion) dated Oct. 9, 2009.
Peachey et al., "Assessment of Opioid Dependence with Naloxone," British Journal of Addiction (1988) 83(2), 193-201.
Philippe et al., "Mu opoid receptor expression is increased in inflammatory bowel diseases: implications for homeostatic intestinal inflammation". GUT, vol. 55, No. 6, pp. 815-823 (2006).
Physician's Desk Reference (2001) see "Oxycontin," pp. 2697-2701.
Physician's Desk Reference (2001) see "Revia," pp. 1146-1149.
Physician's Desk Reference 48th ed.; 1994; "Talwin," 2120-2121, Montvale, NJ.
Pitts et al., "Antinociceptive and Response Rate-Altering Effects of Kappa Opioid Agonists, Spiradoline, Enadoline and U69,593, Alone and in Combination with Opioid Antagonists in Squirrel Monkeys"; J of Pharm and Exper Thera (1994) vol. 271, No. 3, pp. 1501-1508.
Poole et al., "The Effect of Sustained-Release Morphine on Breathlessness and Quality of Life in Severe Chronic Obstructive Pulmonary Disease," Am J Respir Crit Care Med, vol. 157, pp. 1877-1880 (1998).
Portenoy et al., "Breakthrough pain: characteristics and impact in patients with cancer pain," PAIN, pp. 129-134 (1999).
Portenoy et al., "Breakthrough pain: definition, prevalence and characteristics," PAIN, vol. 41, pp. 273-281 (1990).
Press Release "International Patent Application to Be Published on Abuse-Resistant Pain Reliever Being Developed by Perdue Pharma"; Aug. 8, 2001.
Preston et al., "Abuse liability and studies of opioid agonist-antagonists in humans"; Drug and Alcohol Dependence (1991) vol. 28, pp. 49-82.
Preston et al., "Buprenorphine and Naloxone alone and in combination in Opioid-dependant Humans"; Psychopharmacology (1988), vol. 94, pp. 484-490.
Preston et al., "Differential Naltrexone Antagonism of Hydromorphone and Pentazocine Effects in Human Volunteers"; J of Pharm and Ezper Thera (1993) vol. 264, No. 2 pp. 813-823.
Preston et al., "Effects of Sublingually given naloxone in Opioid-dependant human volunteers"; Drug and Alcohol Dependence (1990) vol. 25, pp. 27-34.
Rapaka et al., "Discovery of Novel Opioid Medications"; NIDA Research Monograph 147 (1995) p. 55-83.
Reents et al., "Naloxone and Naltrexone* Application in COPD," Chest, vol. 93, No. 1, pp. 217-219 (1988).
Reimer et al., "Meeting the challenges of opioid-induced constipation in chronic pain management—a novel approach," Pharmacology, 83:10-17 (2009).
Rentz et al., "Validation of the Bowel Function Index to detect clinically meaningful changes in opioid-induced constipation," Journal of Medical Economics (JME), 12(0):371-383 (2009).
Resnick et al., "Naloxone Precipitated Withdrawal: A Method for Rapid Induction Onto Naltrexone," Clinical Pharmacology and Therapeutics, vol. 21, No. 4, pp. 409-413; received for publication Nov. 16, 1976.
Revicki et al., "Recommendation on health-related quality of life research to support labeling and promotional claims in the United States" QOL Research 9(8): 887-900 (2000).
Richter et al., "Clinical Investigation on the Development of Dependence during Oral Therapy with Tramadol"; Arzniem-Forsch/Drug Res. 35 (No. II)(1985)pp. 1742-1744.
Rosen et al., "A Pilot Study of Dextromethorphan in Naloxone-Precipitated Opiate Withdrawal"; European J. of Pharm. (1996) vol. 307, pp. 251-257.
Rosen et al., "The effect of Lamotrigine on Naloxone-precipitated Opiate withdrawal"; Drug and Alcohol Dependence (1998) vol. 52, pp. 173-176.
Rosow et al., Reversal of opioid-induced bladder dysfunction by intravenous naloxone and methylnaltrexone, Clin Pharm & Ther. vol. 82, No. 1, pp. 48-53 (2007).
Rote Liste 2004, Jan. 1, 2004; Frankfurt/Main, vol. 2004, pp. 05001-05033.
Sandner F., "Hope for patients with chronic pain: naloxone and oxycodone fixed combination offers analgesia and prevention of constipation also during sleep," J of Pham and Therapy, vol. 16; No. 6; pp. 179-180 (2007).
Sandner-Kiesling et al., "Long-term efficacy and safety of combined prolonged-release oxycodone and naloxone in the management of non-cancer chronic pain," International Journal of Clinical Practice, 64(6):763-774 (2010).
Schenck et al., "Severe, childhood-onset, idiopathic, life-long insomnia responding selectively to opiate therapy: case report with 19 year follow-up," Sleep Med., vol. 2, No. 6, pp. 531-536 (2001).
Schenck et al., Letter to the Editor, Sleep Med., vol. 4, No. 3, p. 251 (2003).
Schmidt, W.K. "Alvimopan (ADL 8-2698) Is a Novel Peripheral Opioid Antagonist," The American Journal of Surgery, 182 (Suppl. to Nov. 2001) 27S-38S (2001).
Schuh et al., "Buprenorphine, Morphine and Naloxone Effects during Ascending Morphine Maintenance in Humans"; J. Pharm and Exper Thera (1996) vol. 278, 2, pp. 836-846.
Schuh et al., "Onset, Magnitude and Duration of Opioid Blockade Produced by Buprenorphine and Naltrexone in Humans"; Psychopharmacology (1999) vol. 145, pp. 162-174.
Schutter et al., "Innovative pain therapy with a fixed combination of prolonged-release oxycodone/naloxone: a large observational study under conditions of daily practice," Current Medical Research and Opinion, 26(6):1377-1387 (2010).
Shen et al., "Ultra-Low Doses of Naltrexone or Etorphine Increase Morphine's Antinocieceptive Potencey and Attenuate Tolerance/Dependence in Mice," Brain Research (1997), 757:176-190.
Shin Yakuzaigaku Soron (3rd revised edition), 1987, p. 148-151.
Simpson et al., "Fixed-ratio combination oxycodone/naloxone compared with oxycodone alone for the relief of opiod induced constipation in moderate-to-severe non-cancer pain," Current Medical Research and Opinion (CMRO), 24(12):3503-3512 (2008).
Smith et al., "Low-dose naltrexone as a treatment for active Crohn's disease," AGA Abstracts, S1397, XP009095749, p. A-218 (2006).
Smith et al., "Low-dose naltrexone therapy improves active Crohn's disease," The American Journal of Gastroenterology, vol. 102, No. 4 pp. 820-828 (2007).
Smith et al., "Single and multiple-dose pharmacokinetic evaluation of oxycodone and naloxone in an opioid agonist/antagonist prolonged-release combination in healthy adult volunteers," Clinical Therapeutics, 30(11):2051-2068 (2008).
Smith et al., "Prolonged-release oxycodone/naloxone tablets: Dose-proportional pharmacokinetics (abstract PW 256)," Presented at the 12th World Congress on Pain, International Association for the Study of Pain (IASP), Glasgow, Scotland, UK (MIS 4790606), Aug. 17-22, 2008.
Stevens et al., Nonspecific Excitatory Effects of Morphine: Reverse-Order Precipitated Withdrawal and Dose-Dose Interactions: Psychopharmacology (1981) vol. 75, pp. 210-211.
Stine et al., "Reduction of Opiate Withdrawal-like Symptoms by Cocaine Abuse during Methadone and Buprenorphine Maintenance"; Am. J. Drug and Alcohol Abuse (1994) vol. 20, 4, pp. 445-458.

(56) References Cited

OTHER PUBLICATIONS

Stine et al., "Use of Drug Combinations in Treatment of Opioid Withdrawal"; J. Clinical Psych. (1992) vol. 12, No. 3, pp. 203-209.
Stoller et al., "Effects of buprenorphine/naloxone in opioid-dependent humans" Psychopharmacology (2001) vol. 154, pp. 230-242.
Strain et al., "Acute Effects of Buprenorphine, hydromorphone and naloxone in methadone-maintained volunteers"; J. Pharm and Exper Thera (1992) vol. 261, No. 3, pp. 985-993.
Strain et al., "Effects of buprenorphine versus buprenorphine/naloxone tablets in non-dependent opioid abusers"; Psychopharmacology (2000) vol. 148, pp. 374-383.
Strain et al., "Opioid antagonist effects of dezocine in opioid-dependent humans"; Clin Pharm and Thera (1996) vol. 60, No. 2, pp. 206-217.
Strain et al., "Precipitated Withdrawal by Pentazocine in Methadone-Maintained Volunteers"; J. Pharm and Exper Thera (1993) vol. 267, No. 2, pp. 624-634.
Sunshine et al., "Analgesic Efficacy of Pentazocine Versus a Pentazocine-Naloxone Combination Following Oral Administration," Clin. J. Pain (1988), 4:35-40.
Suzuki et al., "Morphine conditioned place preference after chronic treatment with naloxone in the rat"; Research Communications in Substance Abuse (1991) vol. 12., No. 3., pp. 119-131.
Sykes "An investigation of the ability of oral naloxone to correct opioid-related constipation in patients with advanced cancer," Palliative Medicine (1996), 10:134-144.
Sykes "Oral naloxone in opioid-associated constipation," Lancet (1991) vol. 337 p. 1475.
Sykes, N.P., "Using Oral Naloxone in Management of Opioid Bowel Dysfunction," in Handbook of Opioid Bowel Syndrome, Chapter 9, (Yuan, C.-S. ed., The Haworth Medical Press 2005).
Tai et al., "Naltrexone: An Antagonist Therapy for Heroin Addiction"; NIDA (1997).
Trzepacz et al., "Response to Opioids in Three Patients with Restless Legs Syndrome," Am. J. Psychiatry, vol. 141, pp. 993-999 (1984).
U.S. Appl. No. 10/510,673: Final Office Action dated Jan. 11, 2011, including references cited therein (21 pages).
U.S. Appl. No. 10/510,673: Non-Final Office Action dated Apr. 27, 2010, including PTO Form 892 and references cited therein (17 pages).
U.S. Appl. No. 10/510,673: Non-Final Office Action dated Apr. 15, 2008, including PTO Form 892 and references cited therein (13 pages).
U.S. Appl. No. 10/510,673: Non-Final Office Action dated Jun. 2, 2009, including references cited therein (15 pages).
U.S. Appl. No. 11/570,197: Final Office Action dated Sep. 21, 2010 (18 pages).
U.S. Appl. No. 11/570,197: Non-Final Office Action dated Jun. 4, 2010, including PTO Form 892 (15 pages).
U.S. Appl. No. 11/570,222: Non-Final Office Action dated Oct. 13, 2010 (10 pages).
U.S. Appl. No. 11/574,778: Non-Final Office Action dated Dec. 9, 2010, including PTO Form 892 (13 pages).
U.S. Appl. No. 11/884,288: Non-Final Office Action dated May 12, 2010, including PTO Form 892 (9 pages).
U.S. Appl. No. 12/162,390: Final Office Action dated Dec. 27, 2010, including PTO Form 892 (13 pages).
U.S. Appl. No. 60/290,439, filed May 11, 2001.
Umbricht et al., "Naltrexone shortened opioid detoxification with buprenorphine"; Drug and Alcohol Dependence (1999) vol. 56 pp. 181-190.
Vaccarino et al., "Endogenous Opiates: 1999"; Peptides 21 (2000) pp. 1975-2034.
Vaccarino et al.,"Analgesia Produced by Normal Doses of Opioid Antagonists Alone and in Combination with Morphine", Pain (1989), 36:103-109.
Valoron® Product Information, 1997-2001 (in German, w/ English translation).
Vicodin, Physicians' Desk Reference 48th ed., 1994; pp. 1143-1145.
Vondrackova et al. "Analgesic efficacy and safety of oxycodone in combination with naloxone as prolonged release tablets in patients with moderate to severe chronic pain," Journal of Pain, vol. 9, No. 12 pp. 1144-1154 (2008).
Walsh et al., "Effects of Naltrexone on Response to Intravenous Cocain, Hydromorphone and their Combination in Humans," (1996).
Walters et al., "Successful Treatment of the Idiopathic Restless Legs Syndrome in a Randomized Double-Blind Trial of Oxycodone Versus Placebo," Sleep, vol. 16, No. 4, pp. 327-332 (1993).
Wang et al., "cDNA cloning of orphan opiate receptor gene family member and its splice variant"; FEBS letters 348 (1994) pp. 75-79.
Wang et al., "Crossover and Parallel Study of Oral Analgesics," J. Clin. Pharmacol (1981), 21:162-168.
Wang et al., "Inverse Agonists and neutral antagonists at mu opioid receptor (MOR): possible role of basal receptor signaling in narcotic dependence"; J. Neurochemistry (2001) vol. 77, pp. 1590-1600.
Wang et al., "Rating the Presence and Severity of Opiate Dependence," Clinical Pharmacology and Therapeutics, vol. 16, No. 4, pp. 653-657; received for publication Jan. 21, 1974.
Watkins et al. "Aminotransferase Elevations in Healty Adults Receiving 4 Grams of Acetaminophen Daily" Jama, Jul. 5, 2006 vol. 296 No. 1.
Way et al., "Responsivity to Naloxone during Morphine Dependence"; Annals New York Academy of Sciences, pp. 252-261, (1976).
Weinberg et al., "Sublingual absorption of selected opioid analgesics"; Clin Pharm Thera (1988) vol. 44, No. 3, pp. 335-342.
Weinhold et al., "Buprenorphine Alone and in Combination with Naltrexone in Non-Dependent Humans," Drug and Alcohol Dependence (1992), 30:263-274.
Wells et al., "In vivo Pharmacological Characterization of SoRI 9409, a Nonpeptidic Opioid-Agonist/ -Antagonist that Produces Limited Antinociceptive Tolerance and Attenuates Morphione Physical Dependence"; J. Pharm and Exper Thera (2001) vol. 297, No. 2, pp. 597-605.
Wiesen et al., "The Safety and Value of Naloxone as a Therapeutic Aid," Drug and Alcohol Dependence, 2 (1977) pp. 123-130.
Wikler et al., "N-Allylnormorphine: Effects of single dose and Precipitation of Acute "Abstinence Syndromes" during addiction to morphine, methadone or heroin in man (post addicts)"; J. Pharmacol. Exp. Ther., 109, 8-20 (1953).
Wilkinson "The Dynamics of Drug Absorption, Distribution, and Elimination," Goodman and Gilman's the Pharmacological Basis of Therapeutics, Chapter 1, Pharmacokinetics, copyright page and pp. 3-29 (2001).
Wilmington, Del., PR Newswire; New Data Published Describing Favorable Safety Profile of REVIA (Naltrexone Hydrochloride Tablets) When Used to Treat Alcohol Dependence, Dec. 1997.
Wodak Alex, "Drug Treatment for Opioid Dependence"; Australian Prescriber (2001) vol. 24, No. 1, pp. 4-6.
Woodward et al., "Prolonged-release oxycodone/naloxone tablets: Pharmacokinetics in the elderly (abstract)," Presented at the 12th World Congress on Pain, International Association for the Study of Pain (IASP), Glasgow, Scotland, UK, Abstract PW 255, (MIS 4789067), Aug. 17-22, 2008.
Wright et al., "Acute physical dependence in Humans; repeated naloxone-precipitated withdrawal after a single-dose of methadone"; Drug and Alcohol Dependence (1991) vol. 27, pp. 139-148.
Wyrwich et al. "Further evidence supporting an SEM-based criterion for identifying meaningful intra-individual changes in health-related quality of life" J. Clin. Epidemiol. 52:861-873 (1991).
Yoburn et al., "Opioid Antagonist-induced Receptor Upregulation: Effects of Concurrent Agonist Administration"; Brain Research Bulletin (1994), vol. 33, pp. 237-240.
Yoburn et al., "Supersensitivity to Opioid Analgesics Following Chronic Opioid Antagonist Treatment: Relationship to Receptor Sensitivity"; Pharmacology Bio Beh (1995) vol. 51 No. 2, pp. 535-539.
Yuan et al., "Efficacy of Orally Administered Methylnaltrexone in Decreasing Subjective Effects After Intravenous Morphine", Drug and Alcohol Dependence (1998); 52:161-165.

(56) References Cited

OTHER PUBLICATIONS

Yuan et al., "The Safety and Efficacy of Oral Methylnaltrexone in Preventing Morphine-induced Delay in Oral-Cecal Transit Time", Clinical Trials and Therapeutics (1997), 61:467-475.
Zaks et al., "Naloxone Treatment of Opiate Dependence"; JAMA (1971) vol. 215, No. 13, pp. 2108-2110.
Zech et al., "Validation of World Health Organization Guidelines for Cancer Pain Relief: a 10-year Prospective Study," Pain, Oct. 1995:63(1):65-76.
Zeppetella et al., "Opioids for cancer breakthrough pain: A pilot study reporting patient assessment of time to meaningful pain relief," J of Pain and Symptom Management, vol. 25, No. 5, pp. 563-567 (2008).
Zhang et al., "Down-Regulation of -Opioid Receptors in Rat and Monkey Dorsal Root Ganglion Neurons and Spinal Cord After Peripheral Axotomy"; Neuroscience (1998) vol. 82., pp. 223-240.
Zhou et al. "A clinical analysis of 18 cases of naloxone treating pruritis due to cholestia, hebei," Modern Journal of Integrated Chinese and Western Medicine, vol. 8, No. 1, p. 43 (1999) (English translation).
Zhu et al., "Naltrexone-precipitated morphine withdrawal in infant rat is attenuated by acute administration if NOS inhibitors but not NMDA receptor antagonists"; Psychopharmacology (2000) vol. 150, pp. 325-336.

PHARMACEUTICAL PREPARATION CONTAINING OXYCODONE AND NALOXONE

CROSS REFERENCE TO RELATED APPLICATIONS

This application is a continuation of U.S. application Ser. No. 15/399,487, filed Jan. 5, 2017, which is a continuation of U.S. application Ser. No. 14/305,785, filed Jun. 16, 2014 (now abandoned), which is a continuation of U.S. application Ser. No. 14/058,068, filed Oct. 18, 2013 (now abandoned), which is a continuation of U.S. application Ser. No. 13/251,172, filed Sep. 30, 2011 (now abandoned), which is a continuation of U.S. application Ser. No. 10/510,674, filed May 23, 2005 (now abandoned), which is a national stage entry of International Application No. PCT/EP03/03540, filed Apr. 4, 2003, which claims priority under 35 U.S.C. §§ 119(a)-(d) and 365(b) of German Application Nos. 10215131.8, filed Apr. 5, 2002, and 10215067.2, filed Apr. 5, 2002, the contents of each of which are incorporated herein by reference in their entireties.

BACKGROUND

The invention concerns a storage-stable pharmaceutical preparation comprising oxycodone and naloxone.

The treatment of severe pain which results from diseases such as cancer, rheumatism and arthritis is central to the treatment of these diseases. The range of pain felt by tumor patients comprises pain of the periosteum and of the bone itself, as well as visceral pain and pain in soft tissues. All such pain forms render the daily life of patients intolerable and often lead to depressive states. Successful pain therapy resulting in a lasting improvement of quality of life for the patients is therefore equally important to the success of a comprehensive therapy, as is the treatment of the actual causes of the disease.

Regarding the importance of a successful pain therapy, the World Health Organization (WHO) has developed a 4-step model for the treatment of patients with tumor pain. This model has proven to be effective in daily routine practice and can be extended to patients suffering from chronic pain or pain forms which result from diseases other than cancer. Depending on the intensity, quality and localization of pain, four steps are distinguished during this therapy, with each next step being indicated if the effect of the pain relief agent used until then is no longer sufficient (Ebell, H. J.; Bayer A. (Ed.): Die Schmerzbehandlung von Tumorpatienten, Thieme 1994 (Supportive Maißnahmen in der Onkologie, Band 3) and Zech, D.; Grond, S.; Lynch, J.; Hertel, D.; Lehmann, K.: Validation of World Health Organisation Guidelines for Cancer Pain Relief: a 10-year prospective study, Pain (1995), 63, 65-76).

According to this 4-step model of the WHO, opioid analgesics take a central role in treating pain. The group of opioid analgesics comprises, besides morphine which represents the prototype of these pharmaceutically active agents, also oxycodone, hydromorphone, nicomorphine, dihydrocodeine, diamorphine, papaveretum, codeine, ethylmorphine, phenylpiperidine and derivatives thereof; methadone, dextropropoxyphene, buprenorphine, pentazocine, tilidine, tramadol and hydrocodone. The ATC-Classification (Anatomical Therapeutic Chemical Classification) of the WHO indicates whether the pharmaceutically active agent represents an opiod analgesic, or not. The pronounced pain-relieving effect of opioid analgesics is due to the imitation of the effect of endogenous, morphine-like acting substances ("endogenous opioids"), whose physiological function is to control the reception and processing of pain stimuli.

Opioids repress the propagation of pain stimuli. Besides the immediate inhibition of neuronal excitatory signal transduction in the spinal cord caused by opioids, an activation of such nerve tracts is relevant, which project form the brainstem into the spinal cord. This activation results in an inhibition of pain propagation in the spinal cord. Moreover, opioids limit the pain reception of the thalamus and by affecting the limbic system they influence the affective pain evaluation.

Opioid receptors are found at different sites in the body. Receptors of the intestine and brain are of particular importance for pain therapy by opioids, especially as their occupation results in different side effects.

Opioid analgesics are considered to be strong agonists if they bind with high affinity to opioid receptors and induce a strong inhibition of pain reception. Substances that also bind with high affinity to opioid receptors, but that do not provoke a reduction of pain reception and which thereby counteract the opioid agonists, are designated as antagonists. Depending on the binding behaviour and the induced activity, opioids can be classified as pure agonists, mixed agonists/antagonists and pure antagonists. Pure antagonists comprise, for example, naltrexone, naloxone, nalmefene, nalorphine, nalbuphine, naloxoneazinen, methylnaltrexone, ketylcyclazocine, norbinaltorphimine, naltrindol, 6-ß-naloxol und 6-ß-naltrexol (Forth W.; Henschler, D.; Rummel W.; Starke, K.: Allgemeine und Spezielle Pharmakologie und Toxikologie, 7. Auflage, 1996, Spektrum Akademischer Verlag, Heidelberg Berlin Oxford).

Due to their good analgesic efficiency compounds such as oxycodone, tilidine, buprenorphine und pentazocine, have been used in the form of medicaments for pain therapy. Medicaments such as Oxigesic® (wherein oxycodone is the analgesic active compound) und Valoron® (wherein tilidine is the analgesic active compound) have proven valuable for pain therapy.

However, use of opioid analgesics for pain therapy might go along with undesirable side effects. Thus, long-term use of opioid analgesics can lead to psychological and physical dependence.

Especially the physical dependence of patients suffering from pain to opioid analgesics leads to the development of tolerance, meaning that upon extended intake, increasingly higher doses of the pain relieving agent have to be taken by the patient, in order to experience pain relief. The euphoregenic effect of opioid analgesics often leads to the abuse of pain relievers. Drug abuse and psychological dependence are a common phenomenon, especially among teenagers. These dangerous effects are especially caused by the substances with strong analgesic capacity, and can range from undesired habituation to fully developed addiction. However, these substances are legitimately used for medical purposes and medicine cannot do without them.

Besides the mentioned disadvantages, the use of potent opioid analgesics for pain therapy often also lead to undesirable side effects, such as obstipation, breath depression, sickness and sedation. Less frequently, the urge or the disability to pass water are observed. Different attempts have been made to counteract the habituation processes and the other side effects occurring during pain therapy. This can be done, e.g. by traditional treatment methods. In the case of drug addiction this might be a drug withdrawal treatment, and in the case of obstipation, this might be done by administration of laxatives.

Other attempts aim at minimizing the addictive and habituation forming potential of opioid analgesics, as well as their other side effects by the administration of antagonists which counteract the opioid analgesic. Such antagonists might be naltrexone or naloxone.

There have been numerous proposals and suggestions, how the application of the aforementioned active compounds could be used to avoid undesired habituation and dependence, or even addiction.

U.S. Pat. Nos. 3,773,955 and 3,966,940 suggested to formulate analgesics in combination with naloxone, in order to prevent dependence-promoting effects such as euphoria and the like, upon parenteral application. The avoidance of side effects such as obstipation has not been addressed.

To limit the parenteral abuse of oral application forms, U.S. Pat. No. 4,457,933 suggested the combination of morphine with naloxone in defined ranges. The avoidance of side effects such as obstipation has also not been mentioned.

U.S. Pat. No. 4,582,835 describes, again in order to avoid abuse, a preparation comprising a combination of buprenorphine and naloxone that is to be administered either parenterally or sublingually.

European application EP 0 352 361 A1 concerns the treatment of obstipation during pain therapy by the oral application of an opioid analgesic and one antagonist, with the antagonist being a pro-drug form of either naltrexone or naloxone. Avoidance of abuse of the opioid analgesic is not an issue in this application.

German patent application DE 43 25 465 A1 also concerns the treatment of obstipation during pain therapy using a preparation which comprises an opioid analgesic and an antagonist. The characterizing feature of this disclosure is that the antagonist which can be naloxone, has to be present in higher amounts than the opioid analgesic which is preferably morphine. This is to ensure that the antagonist unfolds its anti-obstipation effect without reducing the analgesic activity of the agonist. The avoidance of abuse of the opioid analgesic is not an issue in this application.

In order to avoid side effects such as obstipation and breath depression during pain therapy, preparations have been introduced on the market which can be taken orally and comprise an opioid analgesic and the opioid antagonist, naloxone. The medicament Talwin® of Windrop/Sterling comprises pentazocine and naloxone. The medicament Valoron® of Gödeke comprises a tilidine-naloxone combination.

Besides the potent analgesic effect, the reduction of addictive potential and the avoidance of side effects, medicaments usable for a successful pain therapy should provide for additional characteristics.

Generally, medicaments have to be formulated in a way that the active compounds are stable as long as possible, under standard storage conditions. Medicaments have also to be formulated in a way that the intended release profiles of the active compounds do not change upon long-term storage.

Additionally, (also in the case of agonist/antagonist-combinations) the release profile of each single active compound should be selectable as required. The measures applied in order to achieve this should not hamper or even prevent that the release profiles of additional active compounds (e.g. in the case of combinations of different active compounds) can be chosen as required. Consequently, there should be no mutual dependency of the release profiles.

Medicaments suitable for pain therapy should either contain the active compounds in such amounts or be formulated in such ways that they have to be taken by the patients only rarely. The easier the application scheme for a pain reliever is, and the more evident it is for the patient why and how often he should take which tablet, the more exactly he will adhere to the physician's orders. The necessity to take the pain reliever only infrequently, will result in a high willingness of the patient to take the pain reliever (compliance).

Through the use of so called sustained-release formulations, i.e. formulations of medicaments from which the active compounds are released over an extended period of time, it has been tried to lower the frequency by which pain relieving medicaments have to be taken, and thereby to increase the compliance of patients. Such sustained-release formulations also make sense in that the sustained release of an opioid analgesic reduces the addictive potential of this active compound.

This is due to the fact that the addictive potential of an active compound is not defined by the compound itself, but rather by the way it is administered and the pharmacodynamics resulting therefrom. Besides the psychotropic effect of an opioid, the rate by which the brain encounters an opioid, is more decisive criterion for the risk of dependency than the active compound itself (Nolte, T.; STKZeitschrift für angewandte Schmerztherapie, 2001, Vol. 2).

The medicament Oxigesic® of Purdue is a preparation from which the opioid analgesic oxycodone is released in a sustained manner. cDue to this formulation, the frequency by which the medicament has to be taken as well as the addictive potential is lowered, however the side effects remain and the danger of developing addiction cannot be excluded, as Oxigesic® does not contain opioid-antagonists.

According to the already mentioned European patent application EP 0 352 361 A, neither the opioid analgesic nor the antagonist are formulated to be released in a sustained manner. Accordingly, the time period during which such preparations are effective is limited and preparations have to be taken multiple times per day. The desired compliance of the patient is not achieved. This application also does not disclose the advantages of formulations of preparations that are characterized by a time-stable and independent release of the active compounds. The storage stability of such preparations is also not addressed by this disclosure.

German patent application DE 43 25 465 A1 discloses formulations according to which obstipation occurring during pain therapy is prevented by the sustained release of the opioid agonist while the antagonist, which is present in excess must not be released in a sustained manner. Due to the high First-Pass-Effect of naloxone, comparably large amounts of this compound have therefore to be used. This application discloses neither the advantages nor the formulations of preparations, which are characterized by time-stable and independent release of the active compounds. The storage stability of such preparations is also not an issue of this disclosure. A doctor using preparations according to this disclosure has therefore to carry out extensive titration experiments each time he wants to increase the dosage.

The company Gödeke offers, under the trademark Valoron®, a pain reliever that comprises a tilidine-naloxone-combination. According to the product literature, a formulation is used from which both active compounds are released in a sustained manner. The matrix used comprises a relevant part of water-swellable material (HPMC) and has therefore to be considered as a swellable (and possibly partially erosive) diffusion matrix. A disadvantage of this known formulation is that tilidine and naloxone, given identical mass ratios but different absolute amounts, show different release profiles. The release rates of the agonist and the antagonist are not independent from each other, which is probably due to the sustained release formulation used. Accordingly, it is necessary for the physician to carry out extensive titration experiments for each individual patient if he wants to increase the dosage even though he does not change the mass ratio of tilidine:naloxone, as he cannot assume that the release profiles of both components will remain constant. The range of therapeutically usable amounts of the analgesic that are available to the doctor is therefore limited.

DETAILED DESCRIPTION OF THE INVENTION

Figure 1:
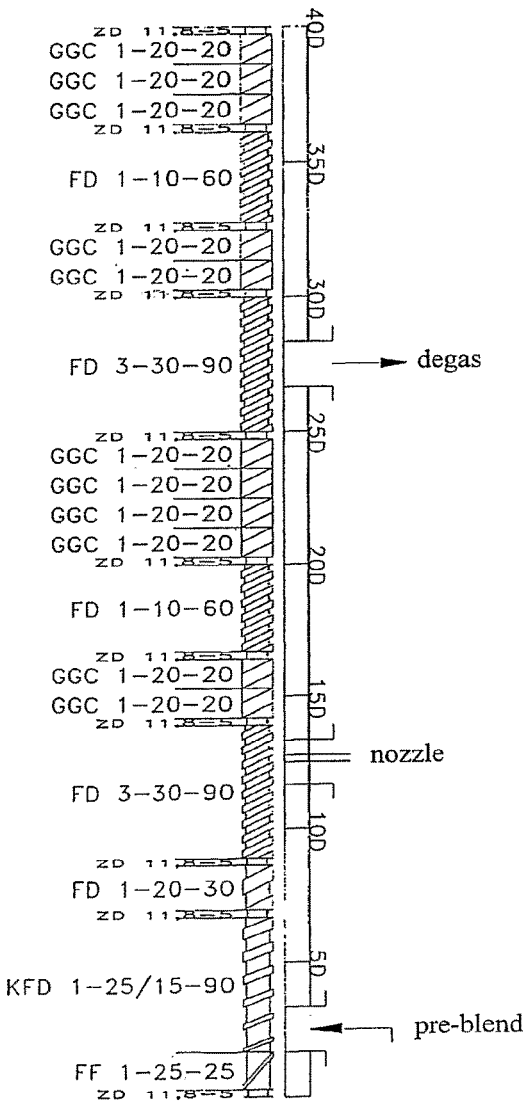
FIG. 1: Screw geometry of the extruder of Example 2.

It is one of the objectives of the present invention to provide a pharmaceutical preparation for pain therapy that, given a high analgesic activity, is characterized by a reduced abuse potential and reduced side effects, said preparation also being characterized by a reduced administration frequency and therefore providing increased compliance, as well as the ability for individual adaptation of the dosage for each patient. A further objective of the present invention is to provide formulations for pharmaceutical preparations usable in pain therapy that make sure that the active compounds of said pharmaceutical preparations are stable over a long storage time, and that the release of the active compounds remain reproducibly invariant and independent from each other even after long-term storage.

The feature combination of the independent claim serves to attain these, and further objectives which can be noted from the ensuing description of the invention. Preferred embodiments of the invention are defined in the subclaims.

According to the invention, the objectives are attained by providing a storage-stable pharmaceutical preparation comprising oxycodone and naloxone wherein said preparation is formulated such that the active compounds are released in a sustained, invariant and independent manner.

By the combination of oxycodone (in an analgesically effective amount) and naloxone it is ensured that preparations according to the invention show an efficient analgesic activity and that at the same time, common side effects such as obstipation, breath depression and development of addiction are suppressed, or at least significantly reduced. The matrix formulation, which is stable over extended periods of time, ensures permanently that agonist as well as antagonist are always released in predetermined percentages and that their release rates do not influence each other. Thereby, abuse of the medicament, which requires that the oxycodone can selectively be extracted from the formulation, is prevented. The formulation according to the invention disables selective extraction of the agonist from the preparation without the corresponding amount of the antagonist, independent of the absolute and relative amounts of agonist and antagonist chosen.

Moreover, the formulation of a medicament according to the invention ensures that, given identical relative amounts, the active compounds show equal release profiles, independent of the absolute amount present. Such an independent release behavior provides a wide range of useable absolute amounts of the analgesic active substance to the physician, given that the optimal agonist/antagonist ratio is known. Thus, it is possible to comfortably adjust the dosage for each individual patient, either by a step-wise dosage increase or, if necessary, a step-wise dosage reduction. This ability to adjust the dosage for the individual patient is extremely useful from a medical point of view.

The characterizing features of the present invention, which comprise the sustained, invariant and independent release of the active compounds ensure additionally that pharmaceutical preparations produced according to the invention are characterized by a low administration frequency, so that high patient compliance is achieved. Furthermore, preparations according to the invention allow the doctor to adjust the dosage for individual patients. Preparations according to the invention enable use over a broad range with respect to the useable absolute amounts of the active compounds and ensure that the active compounds, even after long-term storage, become effective with equal release profiles.

According to the present invention, sustained release of active compounds means that pharmaceutically active substances are released from a medicament over a longer period of time than they are from known formulations for immediate release. Preferably, the release takes place over a time period of two to twenty four hours, of two to twenty hours, especially preferred over a time period of two to sixteen hours or two to twelve hours, with the specifications satisfying the legal and regulating requirements.

According to the invention, formulations of medicaments that ensure such a sustained release of the active compounds from the preparation, are designated as retard formulations, as sustained release formulations or as prolonged release formulations. In the context of the instant invention, "sustained release" does not mean that the active compounds are released from the formulation or the medicament in a pH-dependent manner. According to the invention, the release of the active compounds rather occurs in a pH-independent manner. According to the invention, the term "sustained release" refers to the release of active compounds from a medicament over an extended period of time. It does not imply the controlled release at a defined place; therefore, it does not mean that the active compounds are either released only in the stomach, or only in the intestine. (Of course, such a release at a defined place could individually be achieved by, e.g., enteric coating of the medicament. However, this presently seems not to be advantageous.)

According to the invention, "independent release" means that, given the presence of at least two active compounds, a change of the absolute amount of one compound does not influence the release profiles of the other compounds so that the release profiles of the other compounds are not changed. For formulations according to the invention such an independent release behaviour is independent of the pH value, for which the release is measured, or of the production process. The pH independency particularly applies to the acidic range, i.e. for pH values <7. The release profile (or release behaviour) is defined as the change of the release of the active compound from the formulation with time, with the amount of each active compound released provided in percents of the total amount of the active compound. The release profile is determined by known tests.

Specifically, this means that for example the release profile of oxycodone, as it is observed for an oxycodone/naloxone-combination with 12 milligrams oxycodone and 4 milligrams naloxone, does not change, if a corresponding preparation with the same formulation contains 12 milligrams oxycodone, but 6 milligrams naloxone.

The independent release feature preferably refers to the situation where preparations of substantially equal composition are compared for the release profile. Preparations of substantially equal composition have different amounts of the active compounds but are otherwise basically the same with respect the components of the composition which essentially influence the release behaviour.

If e.g. the above-mentioned preparations are compared (with the first preparation comprising 12 mg oxycodone and 4 mg naloxone and the second preparation comprising 12 mg oxycodone and 6 mg naloxone) both preparations, provided that they have the same total weight, will provide for the same release profile for oxycodone and naloxone if the difference in the naloxone amount is replaced by a component in the formulation that typically does not influence the release behaviour. As shown in the Example section, the difference in the amount of naloxone my[sic] be replaced by a typical pharmaceutically inert filler such as lactose without changing the release profiles.

The person skilled in the art is well aware that if the amount of the active compound in which two preparations differ is replaced by a substance that is essential for the release behaviour of the formulation, such as ethylcellulose or a fatty alcohol, differences in the release behaviour may occur. Thus, the independent release feature preferably applies to formulations that have different amounts of the active compounds but are otherwise identical or at least highly similar with respect to the components that essentially influence the release behaviour (given that formulations of the same total weight are compared).

According to the invention, "invariant release behaviour" or "invariant release profile" is defined so that the percentage of the absolute amount of each active compound released per time unit does not significantly change and remains sufficiently constant (and thus does not substantially change) if absolute amounts are changed. Sufficiently constant percentages mean that the percentage released per time unit deviates from a mean value by not more than 20%, preferably by not more than 15% and especially preferably by not more than 10%. The mean value is calculated from six measurements of the release profile. Of course, the amount released per time unit has to satisfy the legal and regulatory requirements.

Specifically, this means for example that given an oxycodone/naloxone combination of 12 mg oxycodone and 4 mg naloxone, during the first 4 hours 25% oxycodone and 20% naloxone are released. If the oxycodone/naloxone combination instead contains 24 mg oxycodone and 8 mg naloxone, during the first 4 hours also 25% oxycodone and 20% naloxone will be released. In both cases the deviation will not be more than. 20% from the mean value (which in this case is 25% oxycodone and 20% naloxone).

As outlined for the independent release behaviour, the invariant release feature also preferably refers to a situation where preparations of substantially equal composition are compared. Such preparation differ with respect to the amount of the active compounds, but are of the same or at least highly similar composition with respect to the release-influencing components of the preparation. Typically, the difference in the amount of an active compound will be replaced by the amount of a pharmaceutical inert excipient which does not substantially influence the release behavior of the preparation. Such a pharmaceutical excipient may be lactose, which is a typical filler in pharmaceutical preparations. The person skilled in the art is well aware that the invariant release feature may not apply to preparations where the difference in the amount of an active compound is replaced by substances that are known to essentially influence the release behaviour of the preparation, such as ethylcellulose or fatty alcohols.

In the Example section it is set out that if one preparation comprises 20 mg oxycodone and 1 mg naloxone or 20 mg oxycodone and 10 mg naloxone, with the difference in naloxone being replaced by lactose, that the two preparations of identical weight provide for the same release profiles, so that they exhibit a sustained, invariant and independent release behaviour.

According to the invention "storage stable" or "storage stability" means that upon storage under standard conditions (at least two years at room temperature and usual humidity) the amounts of the active compounds of a medicament formulation do not deviate from the initial amounts by more than the values given in the specification or the guidelines of the common Pharmacopoeias. According to the invention, storage stability also means that a preparation produced according to the invention can be stored under standard conditions (60% relative humidity, 25° C.) as it is required for admission to the market.

According to the invention, "storage stable" or "time stable" also means that after storage under standard conditions the active compounds show release profiles as they would upon immediate use without storage. According to the invention, the admissible fluctuations with respect to the release profile are characterized in that the amount released per time unit fluctuates by no more than 20%, preferably no more than 15% and especially preferably no more than 10%, with respect to a mean value. The mean value is calculated from six measurements of the release profile.

Preferably, the release of the active compounds from a sustained release formulation is determined by the Basket Method according to USP at pH 1.2 or pH 6.5 with HPLC.

Storage stability is preferably determined by the Basket Method according to USP at pH 1.2 with HPLC.

According to the invention, a "non-swellable" or "substantially non-swellable" diffusion matrix is a matrix formulation for which the release of the active compounds is not influenced (or at least not to a relevant degree) by swelling of the matrix (particularly in the physiological fluids of the relevant target sites in the patient's body).

According to the invention, the term "substantially non-swellable" diffusion matrix also refers to a matrix whose volume will increase by approximately 300%, preferably by approximately 200%, more preferably by approximately 100%, by approximately 75% or by approximately 50%, even more preferably by approximately 30% or by approximately 20% and most preferably by approximately 15%, by approximately 10%, by approximately 5% or by approximately 1% in aqueous solutions (and particularly in the physiological fluids of the relevant target sites in the patient's body).

In the context of the present invention, "agonist" or "analgesic" always refers to oxycodone. In the context of the present invention "antagonist" always refers to naloxone.

Preparations produced according to the invention can be applied orally, nasally, rectally and/or by inhalation for use in pain therapy. According to the invention, parenteral application is not envisaged. Especially preferred is a formulation for oral application.

Even though this might not be expressly stated, the term "agonist" or "antagonist" always comprises pharmaceutical acceptable and equally acting derivatives, salts and the like. If, for example, oxycodone or naloxone is mentioned, this also comprises, besides the free base, their hydrochloride, sulfate, bisulfate, tatrate, nitrate, citrate, bitratrate, phosphate, malate, maleate, hydrobromide, hydroiodide, fumarate, succinate and the like.

According to the invention, agonists and antagonists are formulated in a way that they are released from the resulting pharmaceutical preparation in a sustained, independent and invariant manner. This does not mean that the antagonist is in excess compared to the agonist. On the contrary, it is preferred that in formulations comprising an agonist/antagonist combination, that show a release profile in accordance with the invention, the agonist is in excess compared to the antagonist.

The excess of the agonist is defined based on the amount of the unit dosage of the antagonist present in the combination preparation. The extent of the excess of the opioid agonist is usually given in terms of the weight ratio of agonist to antagonist.

In the case of oxycodone and naloxone, preferred weight ratios of agonist to antagonist lie within a weight ratio range of 25:1 at maximum, especially preferred are the weight ratio ranges 15:1, 10:1, 5:1, 4:1, 3:1, 2:1 and 1:1.

The absolute amounts of agonist and antagonist to be used depend on the choice of the active compounds. According to the invention, care has to be taken that agonist and antagonist are released from the pharmaceutical preparation that has been formulated for sustained release, only in an independent and invariant manner.

If oxycodone and naloxone are used for a combination preparation, preferably between 10 and 150 mg, especially preferably between 10 and 80 mg of oxycodone (typical amounts for use) and preferably between 1 and 50 mg naloxone per unit dosage are used.

In other preferred embodiments of the invention, the preparations may comprise between 5 and 50 mg of oxycodone, between 10 and 40 mg of oxycodone, between 10 and 30 mg of oxycodone or approximately 20 mg of oxycodone. Preferred embodiments of the invention may also comprise preparations with between 1 and 40 mg naloxone, 1 and 30 mg naloxone, 1 and 20 mg naloxone or between 1 and 10 mg naloxone per unit dosage.

According to the invention, the ratio between oxycodone and naloxone has to be chosen in such a way that release profiles for both active substances in accordance with the invention are guaranteed and that the agonist can display its analgesic effect while the amount of the antagonist is chosen in such a way that habituation- or addiction-promoting effects and side effects of the agonist are reduced or abolished, without (substantially) affecting the analgesic effect of the agonist. According to the invention, development of habituation and addiction as well as obstipation and breath depression are to be considered as side effects of analgesically effective opioid agonists.

According to the invention, generally common formulations can be used, given that these formulations ensure that the active compounds are released from the preparation in a sustained, independent and invariant manner. According to the invention, those formulations have to be chosen such that the active compounds are storage stable.

Matrix-based retardation formulations may preferably be used as formulations that provide a release of agonist and antagonist in accordance with the invention. According to the invention, especially preferred are formulations based on a substantially non-swellable diffusion matrix. At the moment, formulations with an erosive matrix or a swellable diffusion matrix are not preferred.

According to the invention, the matrix that provides the sustained release of the active compounds, has to be chosen in such a way that the release of the active compounds occurs in a sustained, independent and invariant manner. Preferably such matrices comprise polymers based on ethylcellulose, with ethylcellulose being an especially preferred polymer. Specifically preferred are matrices comprising polymers as they are available on the market under the trademark Surelease®. Particularly preferred is the use of Surelease®E-7-7050

Formulations with a release behavior according to the invention comprise particularly matrices that comprise ethylcellulose and at least one fatty alcohol as the components that essentially influence the release characteristics of the matrix. The amounts of ethylcellulose and the at least one fatty alcohol may significantly vary so that preparations with different release profiles may be achieved. Even though the inventive preparations usually will comprise both of the afore-mentioned components, in some cases it may be preferred that the preparations comprise only ethylcellulose or the fatty alcohol(s) as the release determining components.

Matrices based on polymethacrylate (as, e.g. EudragiteRS30D and EudragiteRL30D) or matrices which comprise relevant amounts of water-swellable material, especially of hydroxyalkyl cellulose derivates such as HPMC, are presently preferably avoided according to the invention.

Matrices that are in accordance with the invention can be used to produce preparations that release active compounds in a sustained, independent and invariant manner and that release equal amounts of the active compounds per time unit. Specifically, this means that in the case of a oxycodone/naloxone combination containing 12 mg oxycodone and 4 mg naloxone, 25% oxycodone and 25% naloxone are released within the first 4 hours. Correspondingly, in the case of a oxycodone/naloxone combination containing 24 mg oxycodone and 8 mg naloxone, 25% oxycodone and 25% naloxone are released during the first 4 hours, with the deviation in both cases being no more than 20% of the mean value (which in this case is 25% oxycodone or naloxone).

Such an equal release behaviour for both active compounds may be desirable for medical aspects.

A preferred embodiment of the invention relates to preparations that release 1% to 40%, preferably 5% to 35%, more preferably between 10% and 30% and even more preferably between 15% and 25% of oxycodone and/or naloxone after 15 minutes. In other preferred embodiments of the invention, 15% to 20%, 20% to 25%, approximately 15%, approximately 20% or approximately 25% of oxycodone and/or naloxone are released after 15 minutes.

Another preferred embodiment of the invention relates to preparations that release between 25% to 65%, preferably between 30% to 60%, more preferably between 35% to 55% and even more preferably between 40% to 50% of oxycodone and/or naloxone after one hour. Preferred embodiments of the invention also relate to preparations that release between 40% to 45%, 45% to 50%, approximately 40%, approximately 45% or approximately 50% of oxycodone and/or naloxone after one hour.

Yet another preferred embodiment of the invention relates to preparations that release between 40% to 80%, preferably between 45% to 75%, more preferably between 45% to 70% and even more preferably between 45% to 50%, 50% to 55%, 55% to 60%, 60% to 65% or 65% to 70% of oxycodone and/or naloxone after 2 hours. Preferred embodiments also comprise preparations that release approximately 45%, approximately 50%, approximately 55%, approximately 60%, approximately 65% or approximately 70% of oxycodone and/or naloxone after 2 hours.

One preferred embodiment of the invention relates to preparations that release 70% to 100%, preferably between 75% to 95%, more preferably between 80% to 95%, and even more preferably between 80% and 90% of oxycodone and/or naloxone after 4 hours. Preferred embodiments of the invention also relate to preparations that release between 80% to 85%, 85% to 90%, approximately 80%, approximately 85% or approximately 90% of oxycodone and/or naloxone after 4 hours.

One preferred embodiment of the invention also relates to preparations that release between 70% to 100%, preferably between 75% to 100%, more preferably between 80% to 95% and even more preferably between 80% to 85%, between 85% to 90% or between 90% to 95% of oxycodone and/or naloxone after 7 hours. Preferred embodiments of the invention also relate to preparations that release approximately 80%, approximately 85%, approximately 90% or approximately 95% of oxycodone and/or naloxone after 7 hours.

Yet another preferred embodiment of the invention relates to preparations that release between 85% to 100%, preferably between 90% to 100%, more preferably between 95% to 100% and even more preferably approximately 95% or 100% of oxycodone and/or naloxone after 12 hours.

According to the invention, formulations that provide a release of the active compounds in accordance with the invention may comprise, besides the matrix forming polymers, fillers and additional substances, such as granulating aids, lubricants, dyes, flowing agents and plasticizers.

Lactose, glucose or saccharose, starches and their hydrolysates, microcrystalline cellulose, cellatose, sugar alcohols such as sorbitol or mannitol, polysoluble calcium salts like calciumhydrogenphosphate, dicalcium- or tricalciumphosphate may be used as fillers.

Povidone may be used as granulating aid.

Highly-disperse silica (Aerosil®), talcum, corn starch, magnesium oxide and magnesium- or calcium stearate may preferably be used as flowing agents or lubricants.

Magnesium stearate and/or calcium stearate can preferably be used as lubricants. Fatty acids like stearic acid, or fats like hydrated castor oil can also preferably be used.

Polyethylene glycols and fatty alcohols like cetyl and/or stearyl alcohol and/or cetostearyl alcohol can also be used as additional substances that influence retardation.

If fillers and additional substances such as dyes and the mentioned lubricants, flowing agents and plasticizers are used, care has to be taken that according to the invention only such combinations together with the matrix forming substance and/or the matrix forming substances are used, which ensure release profiles of the active compounds in accordance with the invention.

All these additional components of the formulations will be chosen in such a way that the release matrix receives the character of a substantially non-water- or non-buffer-swellable and non-erosive diffusion matrix.

According to the invention, a formulation is especially preferred that comprises ethylcellulose or Surelease® E-7-7050 as a matrix-building substance, stearyl alcohol as fatty alcohol, magnesium stearate as lubricant, lactose as filler and povidone as a granulating aid.

Preparations in accordance with the invention can be produced as all common application forms which, on principle, are suitable for retardation formulations and which ensure that the active compounds are released in a manner in accordance with the invention. Especially suitable are tablets, multi-layer tablets and capsules. Additional application forms like granules or powders can be used, with only those applications forms being admissible that provide a sufficient retardation and a release behaviour in accordance with the invention.

Pharmaceutical preparations may also comprise film coatings. However, it has to be ensured that the film coatings do not negatively influence the release properties of the active compounds from the matrix and the storage stability of the active compounds within the matrix. Such film coatings may be colored or may comprise a initial dosage of the active compounds if required. The active compounds of this initial dosage will be immediately released so that the therapeutically effective blood plasma level is reached very quickly.

Pharmaceutical preparations or preliminary stages thereof which are in accordance with the invention can be produced by build-up or break-down granulation. A preferred embodiment is the production by spray granulation with subsequent drying of the granules. Another preferred embodiment is the production of granules by build-up granulation in a drum or on a granulating disk. The granules may then be pressed into e.g. tablets using appropriate additional substances and procedures.

The person skilled in the art is familiar with granulating technology as applied to pharmaceutical technology. The embodiment examples (see below) disclose specific embodiments of the invention. However, it is well within the scope of the person skilled in the art to adapt the parameters of the process in order to achieve specific purposes.

Production of pharmaceutical preparations or preliminary stages thereof, which are in accordance with the invention, by extrusion technology is especially advantageous. In one preferred embodiment, pharmaceutical preparations or preliminary stages thereof are produced by melt extrusion with co- or counter-rotating extruders comprising two screws. Another preferred embodiment is the production by means of extrusion, with extruders comprising one or more screws. These extruders may also comprise kneading elements.

Extrusion is also a well-established production process in pharmaceutical technology and is well known to the person skilled in the art. The person skilled in the art is well aware that during the extrusion process, various parameters, such as the feeding rate, the screw speed, the heating temperature of the different extruder zones (if available), the water content, etc. may be varied in order to produce products of the desired characteristics. The Example section provides for numerous examples of preparations according to the invention that have been produced by extrusion.

The aforementioned parameters will depend on the specific type of extruder used. During extrusion the temperature of the heating zones, in which the components of the inventive formulation melt, may be between 40 to 120° C., preferably between 50 to 100° C., more preferably between 50 to 90° C., even more preferably between 50 to 70° C. and most preferably between 50 to 65° C., particularly if counter-rotating twin screw extruders (such as a Leistritz Micro 18 GGL) are used. The person skilled in the art is well aware that not every heating zone has to be heated. Particularly behind the feeder where the components are mixed, cooling at around 25° C. may be necessary. The screw speed may vary between 100 to 500 revolutions per minute (rpm), preferably between 100 to 250 rpm, more preferably between 100 to 200 rpm and most preferably around 150 rpm, particularly if counter-rotating twin screw extruders (such as a Leistritz Micro 18 GGL) are used. The geometry and the diameter of the nozzle may be selected as required. The diameter of the nozzle of commonly used extruders typically is between 1 to 10 mm, preferably between 2 to 8 mm and most preferably between 3 to 5 mm. The ratio of length versus diameter of the screw of extruders that may be used for production of inventive preparations is typically around 40:1.

Generally, the temperatures of the heating zones have to be selected such that no temperatures develop that may destroy the pharmaceutically active compounds. The feeding rate and screw speed will be selected such that the pharmaceutically active compounds are released from the preparations produced by extrusion in a sustained, independent and invariant manner and are storage stable in the matrix. If e.g. the feeding rate is increased, the screw speed may have to be increased correspondingly to ensure the same retardation.

The person skilled in the art knows that all the aforementioned parameters depend on the specific production conditions (extruder type, screw geometry, number of components etc.) and may have to be adapted such that the preparations produced by extrusion provide for a sustained, independent and invariant release as well as for the afore-mentioned storage stability.

The person skilled in the art can infer from the Examples (see below) that by changing the parameters during extrusion and by changing the composition with respect to the compounds that substantially responsible for the release behavior of the preparations, preparations with different release profiles may be obtained. Thus, the present invention allows to first produce a preparation with a desired release profile for oxycodone and naloxone by e.g. varying the amount of fatty alcohols or the matrix-forming polymer ethylcellulose as well as production parameters such as temperature, screw speed (during extrusion) or pressure power during tablet production.

Once a preparation with the desired release profile has been obtained, the inventive preparations according to the invention allow the person skilled in the art to change the amounts of the preparations with respect to the active compounds as outlined above. Preparations comprising different amounts of the active compounds but of otherwise substantially equal composition, however, will then provide for the features of sustained, invariant and independent release.

The Example section therefore discloses numerous examples showing that preparations with different release profiles may be obtained by changing the amount of e.g. ethylcellulose. Other examples show that once a preparation has been established with desired release profiles, the change in the amount of naloxone will not influence the release behaviour of such preparations if the difference in the amount of the active compound is replaced by pharmaceutically inert excipients such as lactose.

Examples that display highly advantageous embodiments of the invention are set out below. Additionally examples are given that emphasize the advantages of preparations according to the invention compared to common formulations. The examples are not to be interpreted as limiting the possible embodiments of the invention.

The invention can be illustrated by the following embodiments enumerated in the numbered paragraphs below:

1. A storage stable pharmaceutical preparation comprising oxycodone and naloxone characterized in that the active compounds are released from the preparation in a sustained, invariant and independent manner.
2. Preparation according to paragraph 1, characterized in that oxycodone and/or naloxone are present in the form of pharmaceutically acceptable and equally active derivatives such as the free base, salts and the like.
3. Preparation according to paragraph 2, characterized in that that oxycodone and/or naloxone are present as their hydrochloride, sulfate, bisulfate, tatrate, nitrate, citrate, bitatrate, phosphate, malate, maleate, hydrobromide, hydroiodide, fumarate or succinate.
4. Preparation according to one of the preceding paragraphs, characterized in that oxycodone is present in excess referred to the unit dosage amount of naloxone.
5. Preparation according to one of the preceding paragraphs, characterized in that Naloxone is present in an amount range of 1 to 50 mg.
6. Preparation according to one of the preceding paragraphs, characterized in that oxycodone is present in an amount range of 10 to 150 mg, preferably of 10 to 80 mg.
7. Preparation according to one of the preceding paragraphs, characterized in that oxycodone and naloxone are present in weight ratio ranges of maximal 25:1, preferably of maximal 20:1, 15:1, especially preferably of 5:1, 4:1, 3:1, 2:1 or 1:1.
8. Preparation according to one of the preceding paragraphs, characterized in that the preparation comprises substantially a non-swellable and non-erosive diffusion matrix.
9. Preparation according to paragraph 8, characterized in that the diffusion matrix comprises at least ethylcellulose and at. least one fatty alcohol as the components that essentially influence the release behaviour of the active compounds.
10. Preparation according to paragraph 8 or paragraph 9, characterized in that the preparation does not comprise relevant parts of alkaline and/or water-swellable substances, especially of derivatives of acrylic acid and/or hydroxyalkyl celluloses.

11. Preparation according to one of the preceding paragraphs, characterized in that the preparation contains usual fillers and additional substances, especially lubricants, flowing agents, plasticizers and the like.
12. Preparation according to paragraph 11, characterized in that it comprises magnesium stearate, calcium stearate and/or calcium laureate and/or fatty acids, preferably stearic acid as the lubricant.
13. Preparation according to paragraph 11, characterized in that it comprises highly-disperse silica, preferably Aerosil®, Talcum, corn starch, magnesium oxide and magnesium and/or calcium stearate as the flowing agent.
14. A storage stable pharmaceutical preparation comprising oxycodone and naloxone in a substantially non-swellable diffusion matrix, characterized in that the matrix is influenced with respect to its substantial release characteristics by ethylcellulose and at least one fatty alcohol and that the preparation comprises oxycodone and naloxone in a weight ratio of maximal 25:1, preferably maximal 20:1, 15:1, especially preferably of 5:1, 4:1, 3:1, 2:1 or 1:1.
15. Preparation according to paragraph 14, characterized in that oxycodone and naloxone are present in the form of pharmaceutically acceptable and equally active derivatives, such as the free-base, salts, and the like.
16. Preparation according to paragraph 15, characterized in that oxycodone and naloxone are present as hydrochloride, sulfate, bisulfate, tatrate, nitrate, citrate, bitatrate, phosphate, malate, maleate, hydrobromide, hydroiodide, fumarate or succinate.
17. Preparation according to one of paragraphs 14 to 16, characterized in that oxycodone is present in excess referred to the unit dosage amount of naloxone.
18. Preparation according to one of paragraphs 14 to 17, characterized in that naloxone is present in an amount range of 1 to 50 mg.
19. Preparation according to one of paragraphs 14 to 18, characterized in that oxycodone is present in an amount range of 10 to 150 mg, preferably of 10 to 80 mg.
20. Preparation according to one of paragraphs 14 to 19, characterized in that the preparation comprises a substantially non-swellable and non-erosive diffusion matrix.
21. Preparation according to paragraph 20, characterized in that the diffusion matrix comprises at least ethylcellulose and at least one fatty alcohol as the components that essentially influence the release behaviour of the active compounds.
22. Preparation according to paragraph 20 or 21, characterized in that the preparation does not comprise relevant parts of alkaline and/or water-swellable substances, especially of derivatives of acrylic acid and/or hydroxy alkyl celluloses.
23. Preparation according to one of paragraphs 14 to 22, characterized in that the fatty alcohols comprise lauryl, myrestyl, stearyl, cetostearyl, ceryl and/or cetyl alcohol, especially preferably stearyl alcohol.
24. Preparation according to one of paragraphs 14 to 23, characterized in that the preparation comprises usual fillers and additional substances, especially lubricants, flowing agents, plasticizers and the like.
25. Preparation according to paragraph 24, characterized in that it comprises magnesium stearate, calcium stearate and/or calcium laureate and/or fatty acids, preferably stearic acid as lubricant.
26. Preparation according to paragraph 24, characterized in that it comprises highly dispersed silica, preferably Aerosil®, talcum, corn starch, magnesium oxide, magnesium stearate and/or calcium stearate as flowing agent.
27. Preparation according to one of the preceding paragraphs, characterized in that commercially available polymer mixtures which comprise ethylcellulose, preferably Surelease® E-7-7050 are used instead of ethylcellulose.
28. Preparation according to one of the preceding paragraphs, characterized in that the preparation has been formulated for oral, nasal, rectal application or for application by inhalation.
29. Preparation according to one of the preceding paragraphs, characterized in that the preparation is a tablet, pill, capsule, granule and/or powder.
30. Preparation according to one of the preceding paragraphs, characterized in that the preparation or precursors thereof are produced by build-up and/or breakdown granulation.
31. Preparation according to one of paragraphs 1 to 29, characterized in that the preparation or precursors thereof are produced by extrusion.
32. Preparation according to one of the preceding paragraphs, characterized in that the preparation can be stored over a period of at least 2 years under standard conditions (60% relative humidity, 25° C.) in accordance with admission guidelines.

Example 1—Production of Tablets with Different Oxycodone/Naloxone Amounts in a Non-Swellable Diffusion Matrix by Spray Granulation The following amounts of the listed components were used for the production of oxycodone/naloxone tablets according to the invention.

| Preparation (designation) | Oxy/Nal-0 | Oxy/Nal-5 | Oxy/Nal-10 |
|---|---|---|---|
| oxycodone HCl | 20.0 mg | 20.0 mg | 20.0 mg |
| naloxone HCl | — | 5.0 mg | 10.0 mg |
| Lactose Flow Lac 100 | 59.25 mg | 54.25 mg | 49.25 mg |
| Povidone 30 | 5.0 mg | 5.0 mg | 5.0 mg |
| Surelease ® | 10.0 mg solid material | 10.0 mg solid material | 10.0 mg solid. material, |
| Stearyl alcohol | 25.0 mg | 25.0 mg | 25.0 mg |
| Talcum | 2.5 mg | 2.5 mg | 2.5 mg |
| Mg-Stearate | 1.25 mg | 1.25 mg | 1.25 mg |

The Surelease® E-7-7050 polymer mixture used had the following composition.

| Surelease ® |
|---|
| Ethylcellulose 20 cps |
| Dibutylsebacate |
| Ammoniumhydroxide |
| Oleic acid |
| Siliciumdioxide |
| Water |

For the production of tablets oxycodone HCl, naloxone HCl, Povidone 30 and Lactose Flow Lac 100 were mixed in a tumbling mixer (Bohle) and subsequently spray-granulated with Surelease® E-7-7050 in a fluidized bath granulating device (GPCG3). The material was sieved over a Comill 1.4 mm sieve. An additional granulation step was carried out with melted fatty alcohol in a high-shear mixer (Collette). All tablet cores produced by this approach had a weight of 123 mg, based on dry substance.

Example 2—Production of Tablets with Oxycodone and Naloxone in a Non-Swellable Diffusion Matrix by Extrusion The following amounts of the listed components were used for the production of the oxycodone/naloxone tablets according to the invention.

| Preparation (designation) | Oxy/Nal-Exix. |
|---|---|
| oxycodone HCl | 20 mg |
| naloxone HCl | 10 mg |
| Kollidon 30 | 6 mg |
| Lactose Flow Lac 100 | 49.25 mg |
| Ethylcellulose 45 cpi | 10 mg |
| Stearyl alcohol | 24 mg |
| Talcum | 2.5 mg |
| Mg-Stearate | 1.25 mg |

The listed amounts of oxycodone HCl, naloxone HCl, ethylcellulose 45 cpi, Povidone 30, stearyl alcohol and Lactose Flow Lac 100 were mixed in a tumbling mixer (Bohle). This mixture was subsequently extruded with a counter-rotating twin screw extruder of the type Micro 18 GGL (Leistritz AG, Nurnberg, Germany). The temperature of heating zone 1 was 25° C., of heating zone 2, 50° C., of heating zones 3 to 5, 60° C., of heating zones 6 to 8, 55° C., of heating zone 9, 60° C. and of heating zone 10, 65° C. The screw rotating speed was 150 revolutions per minute (rpm), the resulting melt temperature was 87° C., the feed rate was 1.5 kg/h and the diameter of the nozzle opening was 3 mm. The extruded material was sieved with a Frewitt 0.68×1.00 mm sieve. The grinded extrudate was then mixed with talcum and magnesium stearate that had been added over a 1 mm hand sieve and was subsequently pressed into tablets. The extruder has a screw geometry, as shown in FIG. 1.

In comparison to the oxycodone/naloxone tablets which also have the Surelease-based non-swellable diffusion matrix produced by spray granulation (see Example 1), extruded preparations comprise less components.

Example 3—Release Profile of the Oxycodone/Naloxone Tablets from Example 1

The release of the active compounds was measured over a time period of 12 hours, applying the Basket Method according to USP at pH 1.2 using HPLC. Tablets Ox/Nal-0, Ox/Nal-5 and Ox/Nal-10 were tested.

Figure 2:
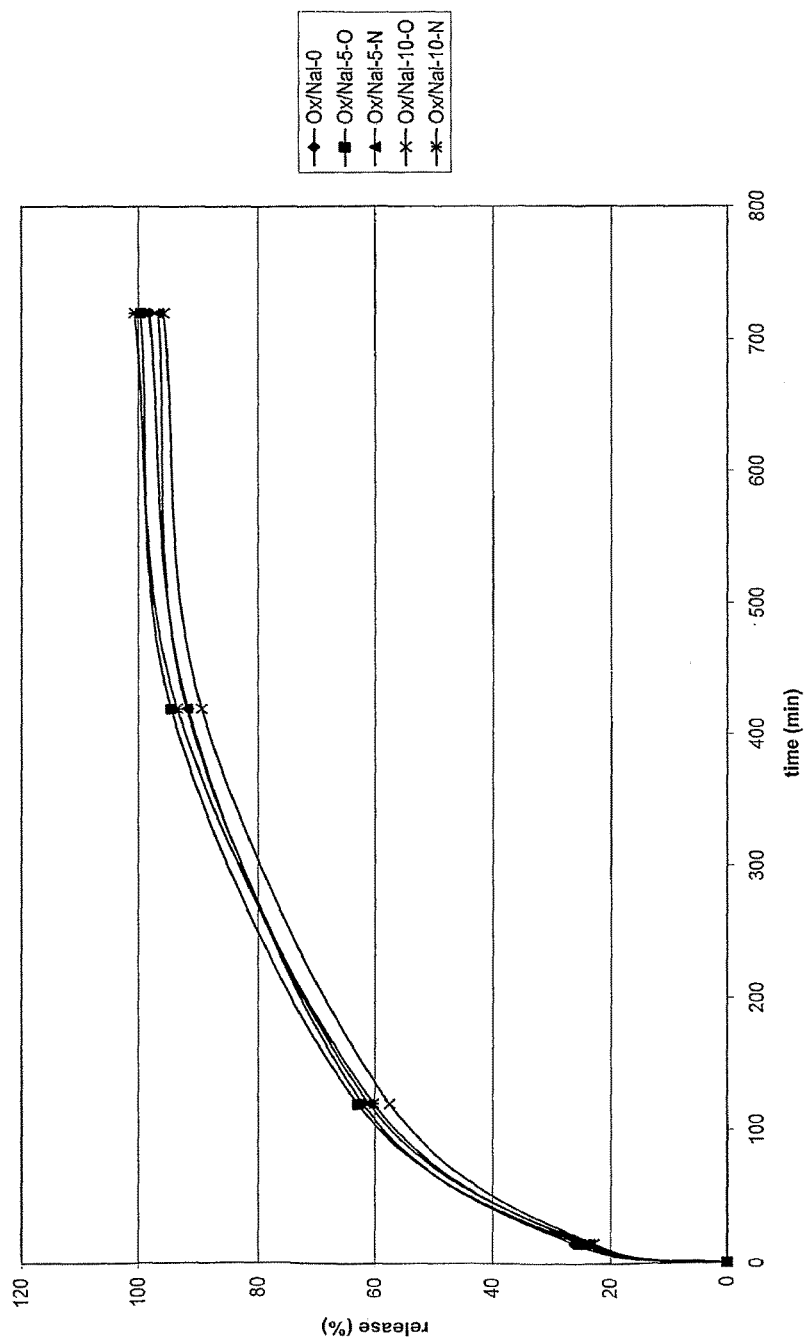
FIG. 2: Release profile of the oxycodone/naloxone tablets from Example 1.

One recognizes from FIG. 2 and the values listed in the Table that in the case of a non-swellable diffusion matrix based on Surelease®, the release rates of different oxycodone amounts, independent of the naloxone amount, remain equal (invariant). Correspondingly, invariant release profiles are observed for naloxone at different oxycodone amounts.

| Time (min) | Ox/Nal-0 Oxy | Ox/Nal-5-O Oxy | Ox/Nal-5-N Nal | Ox/Nal-10-O Oxy | Ox/Nal-10-N Nal |
|---|---|---|---|---|---|
| 0 | 0 | 0 | 0 | 0 | 0 |
| 15 | 26.1 | 24.9 | 23.5 | 22.8 | 24.1 |
| 120 | 62.1 | 63 | 61 | 57.5 | 60.2 |
| 420 | 91.7 | 94.5 | 91.9 | 89.4 | 93.5 |
| 720 | 98.1 | 99.6 | 96.6 | 95.7 | 100.6 |

The release values refer to oxycodone or naloxone (line 2) and are given as percentages. The mean value for the release of naloxone at e.g. 420 min is 92.7%. The maximal deviation at 420 min is 1%. Oxy and Nal stand for oxycodone and naloxone and indicate the active compound which has been measured.

Example 4—Release Profile of Oxycodone/Naloxone Tablets from Example 2 at Different pH-Values The release of active compounds from the tablets was measured over a time period of 12 hours at pH 1.2 or for 1 hour at 1.2 and subsequently for 11 hours at pH 6.5. Release rates were determined by the basket method according to USP using HPLC.

The following release rates were measured for 12 hours at pH 1.2:

| Time (min) | Oxy/Nal-Extr-1,2-O Oxy | Oxy/Nal-Extr-1,2-N Nal |
|---|---|---|
| 0 | 0 | 0 |
| 15 | 24.1 | 24.0 |
| 120 | 62.9 | 63.5 |
| 420 | 92.9 | 93.9 |
| 720 | 96.9 | 98.1 |

The following release rates were measured for 1 hour at pH 1.2 and 11 hours at pH 6.5:

| Time (min) | Oxy/Nal-Extr-6,5-O Oxy | Oxy/Nal-Extr-6,5-N Nal |
|---|---|---|
| 0 | 0 | 0 |
| 60 | 48.1 | 49.2 |
| 120 | 65.0 | 64.7 |
| 240 | 83.3 | 81.8 |
| 420 | 94.1 | 92.3 |

The release rates refer to oxycodone and naloxone (line 2) and are given as percentages. Oxy and Nal stand for oxycodone and naloxone and indicate the active compound measured.

The comparison of the values given in the Tables of Example 4 and the Table of Example 3 make clear that independent of the production process, active compounds are released in equal amounts from the preparations. For example, 89.4% of oxycodone is released from spray-granulated tablets (Ox/Nal-10-tablets, see Example 3) at 420 minutes, while 92.9% is released from extruded tablets (Oxy/Nal-Extr-1.2-O, Example 4) at 420 minutes. The release of oxycodone from extruded tablets thus deviates by 1.1% from the mean value of the release of oxycodone from spray-granulated tablets (91.9% at 420 minutes). 93.5% of naloxone is released from spray-granulated tablets (Ox/Nal-10-tablets, see Example 3) at 420 minutes, while 93.9% is released from extruded tablets (Oxy/Nal-Extr.-1.2-O, Example 4) at 420 minutes. The release of naloxone from extruded tablets thus deviates by 1.3% from 20 the mean value of the release of naloxone from spray-granulated tablets (92.7% at 420 minutes).

Figure 3A:
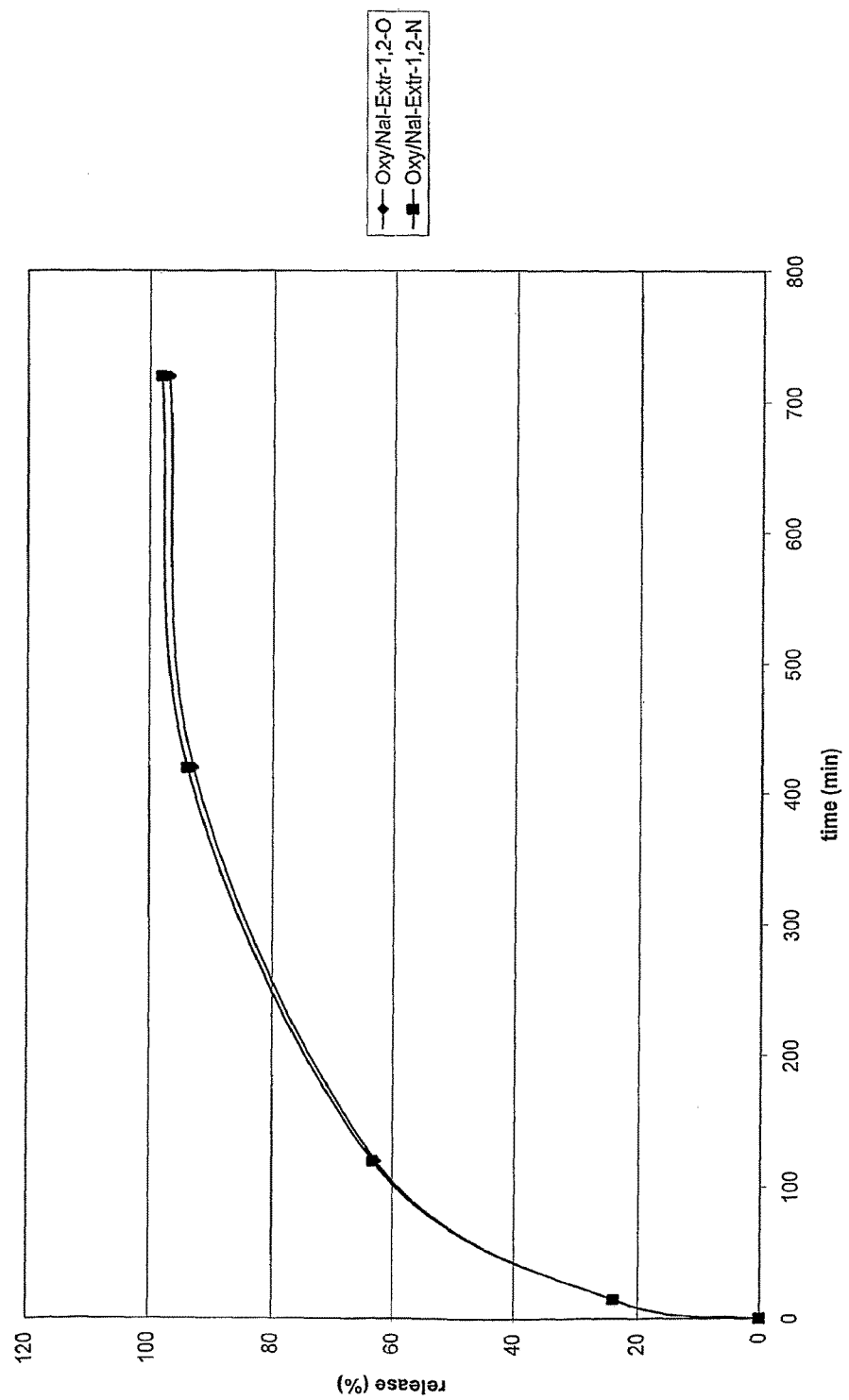
FIG. 3A: Release profile of the oxycodone/naloxone tablets from Example 2 at pH 1.2.
Figure 3B:
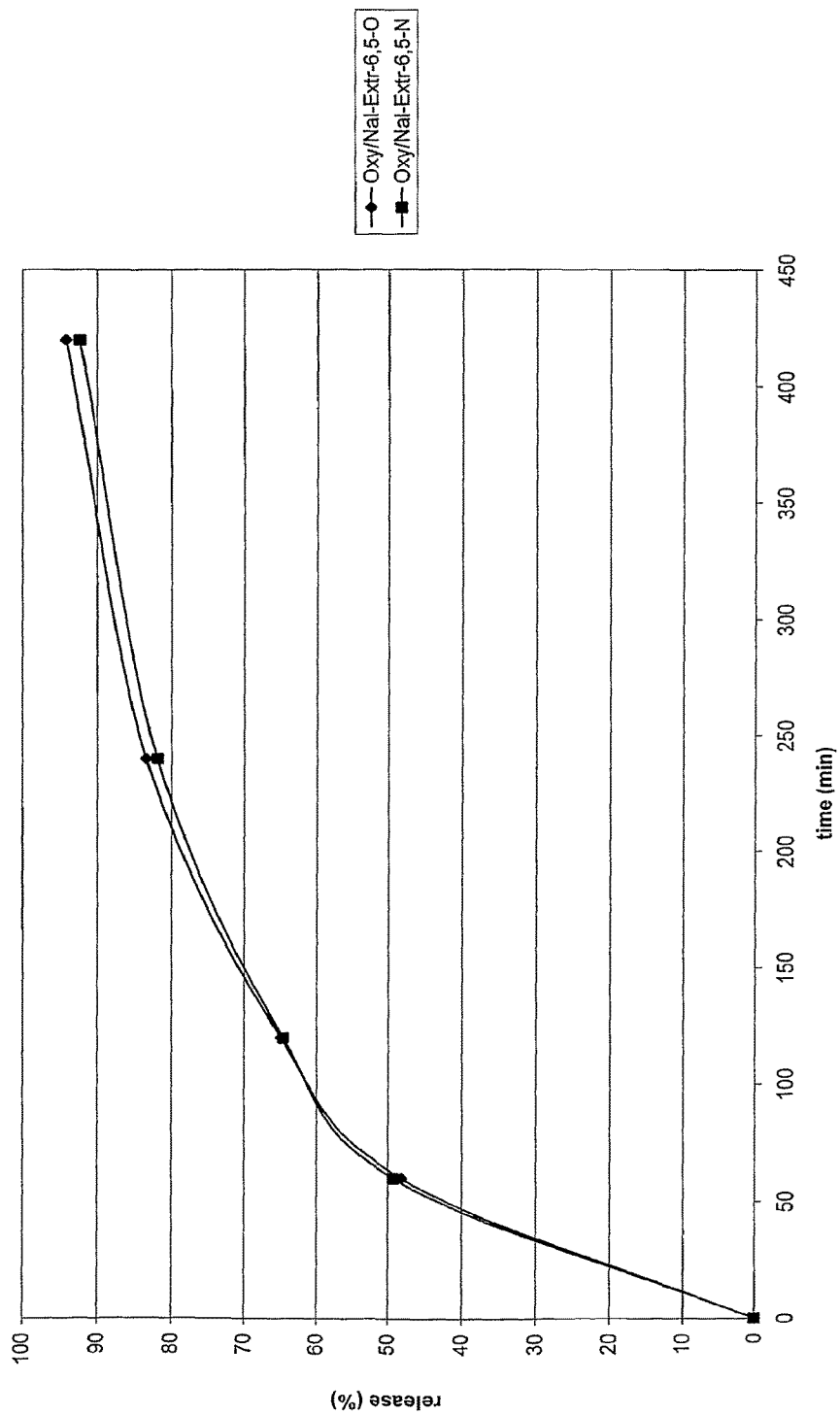
FIG. 3B: Release profile of the oxycodone/naloxone tablets from Example 2 at pH 6.5.

Moreover, one can infer from a comparison of the values of the Tables of Example 4 and from FIGS. 3a and 3b that independent of the pH value at which the release rates have been measured the release of oxycodone and naloxone remain equal and invariant.

Example 5—Comparative Example: Release Behaviour of Valoron® Tablets

The release of the active substances from tablets was monitored over a time period of 7 hours. Valoron® tablets with 50 mg tilidine and 4 mg naloxone (Ti/Nal-50/4) or 100 mg tilidine and 8 mg naloxone (Ti/Nal-100/8) or 150 mg tilidine and 12 mg naloxone (Ti/Nal-150/12) were tested by the Basket Method according to USP for 1 h at pH 1.2 and then for additional 6 h at pH 6.5 using HPLC.

Figure 4A:
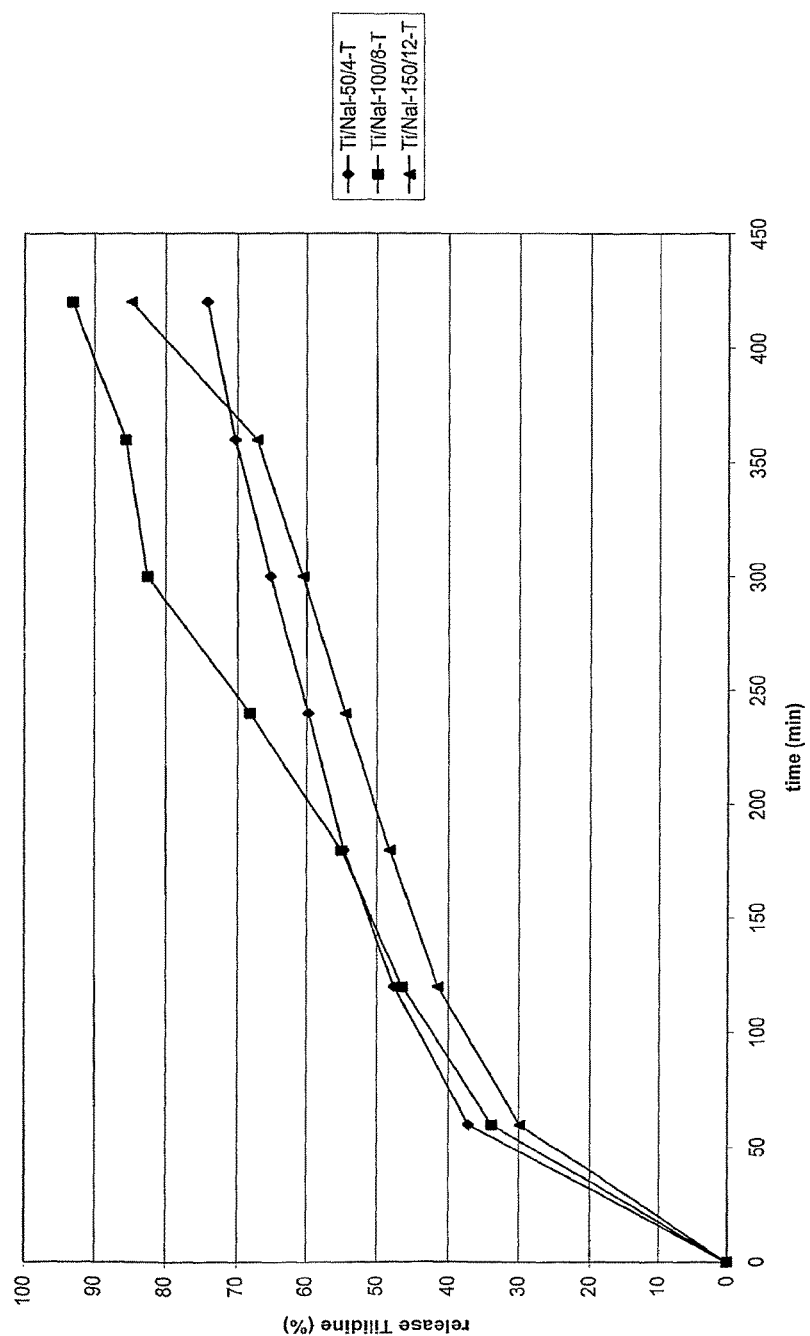
FIG. 4A: Release profile of tilidine from Valoron® tablets with 50 mg tilidine and 4 mg naloxone (Ti/Nal-50/4), 100 mg tilidine and 8 mg naloxone (Ti/Nal-100/8), and 150 mg tilidine and 12 mg naloxone (Ti/Nal-150/12).
Figure 4B:
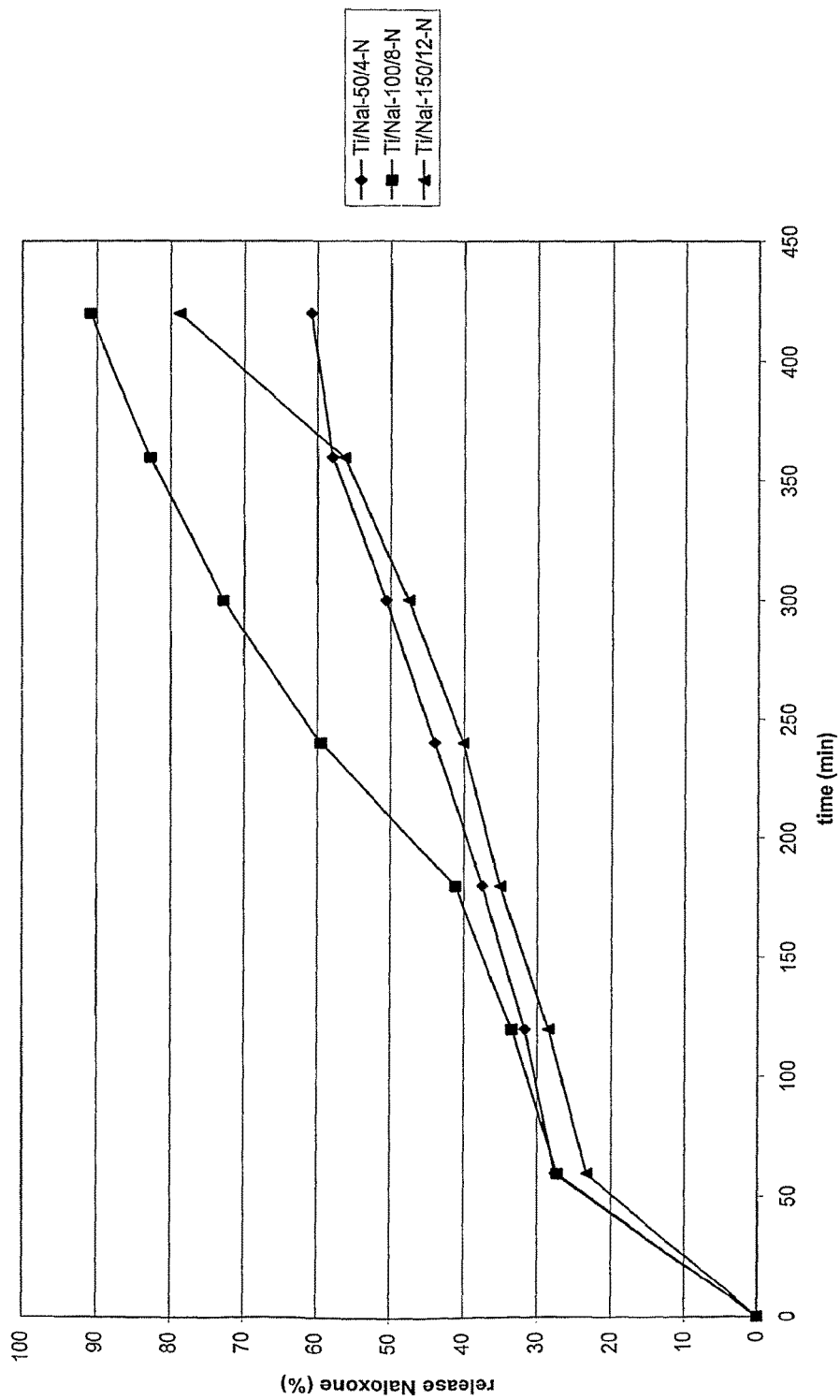
FIG. 4B: Release profile of naloxone from Valoron® tablets with 50 mg tilidine and 4 mg naloxone (Ti/Nal-50/4), 100 mg tilidine and 8 mg naloxone (Ti/Nal-100/8), and 150 mg tilidine and 12 mg naloxone (Ti/Nal-150/12).

One recognizes from FIGS. 4A and 4B and the values listed in the Table that in case of a swellable (and possibly erosive) diffusion matrix with relevant amounts of HPMC, the release of different amounts of tilidine varies significantly and is not invariant for different amounts of naloxone. This applies in turn to naloxone. This means that for this pH the release of the active compounds is not independent of each other.

| Time (min) | Ti/Nal-50/4-T Til | Ti/Nal-50/4-N Nal | Ti/Nal-100/8-T Til | Ti/Nal-100/8-N Nal | Ti/Nal-150/12-T Til | Ti/Nal-150/12-N Nal |
|---|---|---|---|---|---|---|
| 0 | 0 | 0 | 0 | 0 | 0 | 0 |
| 60 | 37.2 | 27.6 | 33.9 | 27.3 | 29.9 | 23.3 |
| 120 | 47.6 | 31.7 | 46.5 | 33.4 | 41.5 | 28.5 |
| 180 | 54.7 | 37.4 | 55 | 41.2 | 48.2 | 35 |
| 240 | 59.7 | 44 | 68.2 | 59.5 | 54.5 | 40.1 |
| 300 | 65.2 | 50.6 | 82.6 | 72.9 | 60.5 | 47.5 |
| 360 | 70.3 | 58 | 85.7 | 82.7 | 67.2 | 56.4 |
| 420 | 74.2 | 60.8 | 93.1 | 90.9 | 84.9 | 78.9 |

The release values refer to tilidine or naloxone (line 2) and are given as percentages. The mean value for the release of naloxone at e.g. 420 min is 78.87%. The maximal deviation at 420 min is 20.4%. Til and Nal stand for tilidine and naloxone and indicate the active compound tested.

Figure 5A:
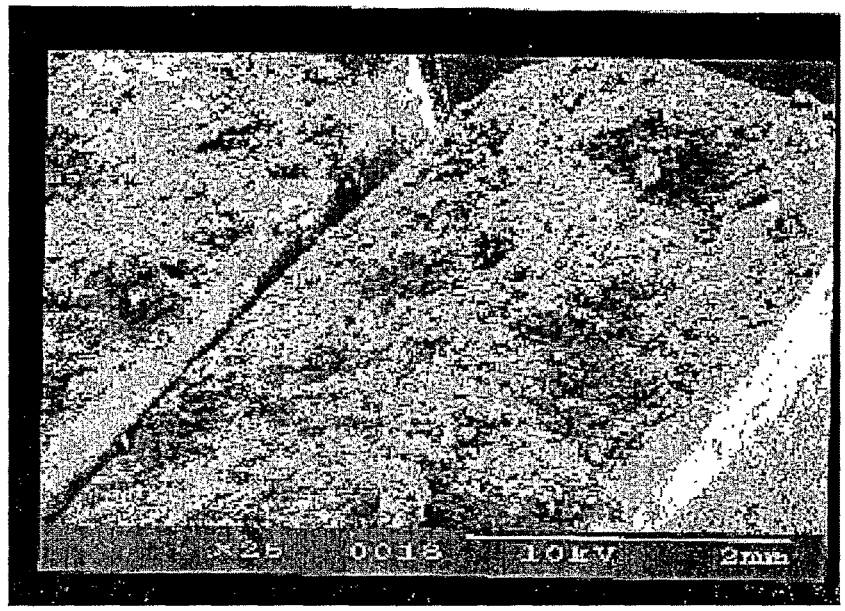
FIG. 5A: Surface of the Ox/Nal-10 tablet at 25× magnification. The voltage was 10 kV. The bar length corresponds to 2 mm.
Figure 5B:
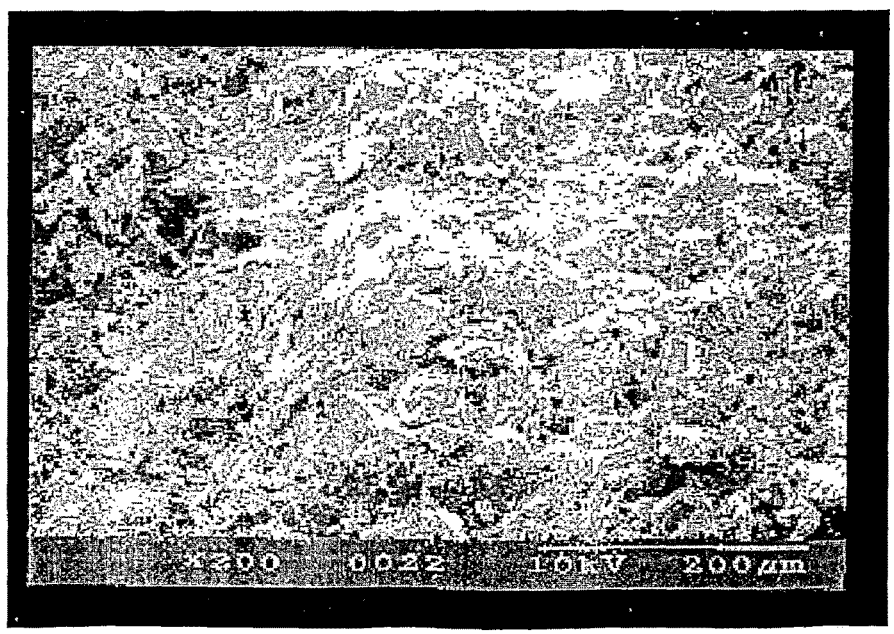
FIG. 5B: Surface of the Ox/Nal-10 tablet at 200× magnification. The voltage was 10 kV. The bar length corresponds to 200 μm.
Figure 6A:
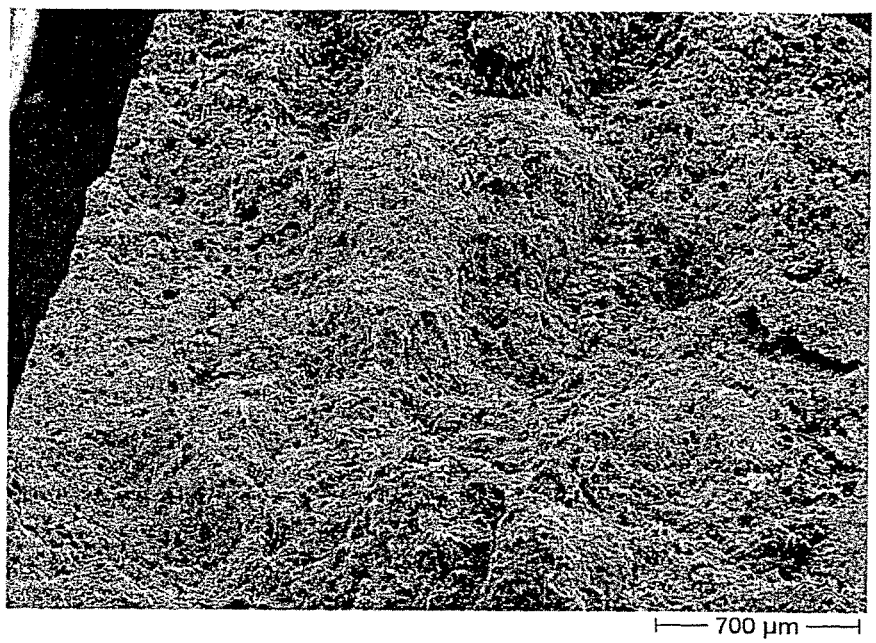
FIG. 6A: Surface of the Oxy/Nal-Extr tablet at 40× magnification. The voltage was 10 kV. The bar length corresponds to 700 μm.
Figure 6B:
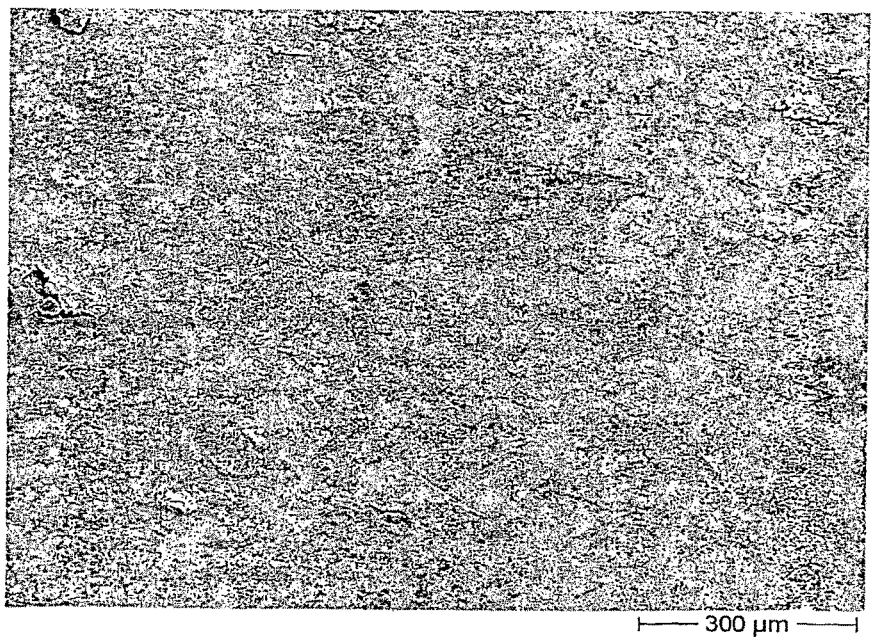
FIG. 6B: Surface of the Oxy/Nal-Extr tablet at 100× magnification. The voltage was 10 kV. The bar length corresponds to 300 μm.
Figure 7A:
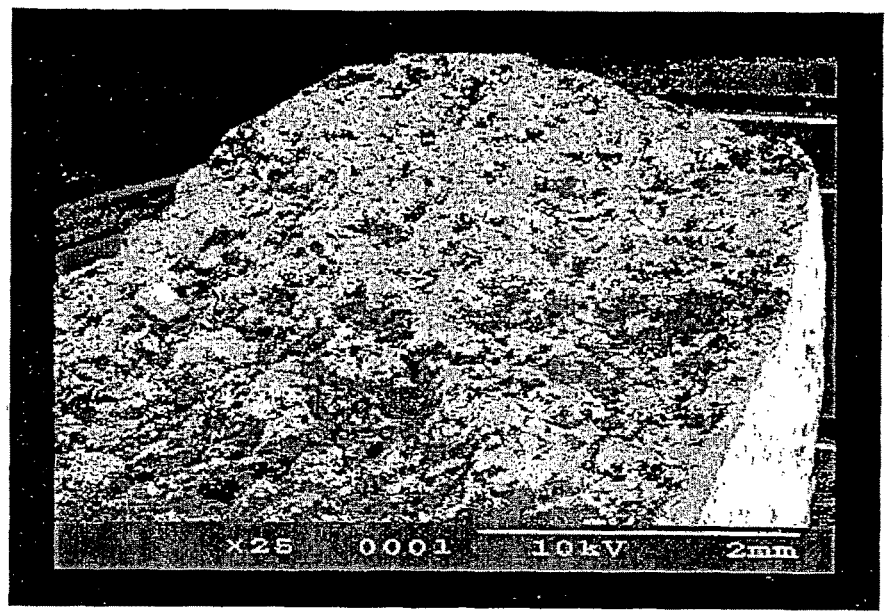
FIG. 7A: Surface of the Valoron® N tablet at 25× magnification. The voltage was 10 kV. The bar length corresponds to 2 mm.
Figure 7B:
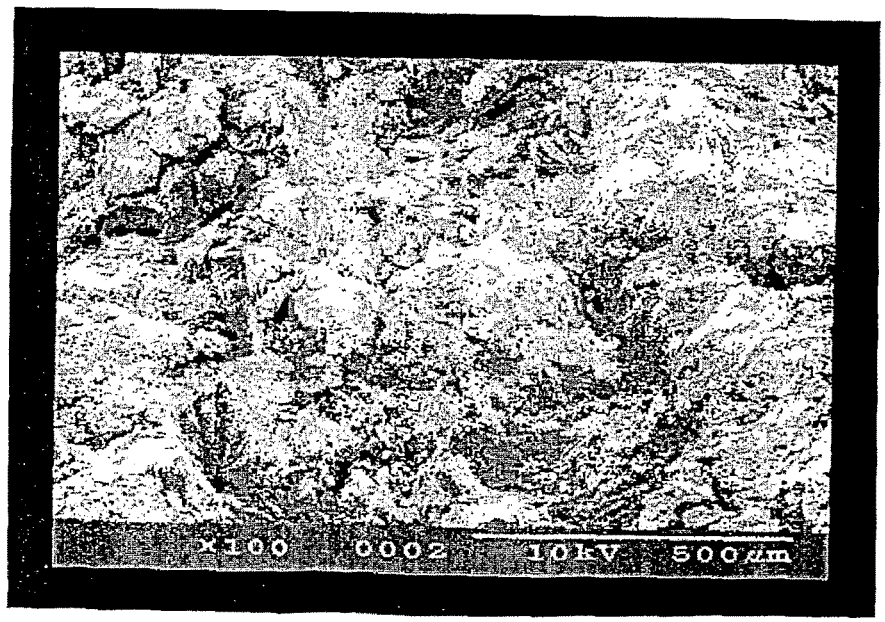
FIG. 7B: Surface of the Valoron® N tablet at 100× magnification. The magnification shows a crystal of tilidine (down left). The voltage was 10 kV. The bar length corresponds to 500 μm.

Example 6—Structure Comparison of Tablets of Examples 1 and 2 with Valoron® N Tablets by Electron Microscopy For electron microscopy tablets were used that comprised 20 mg oxycodone and 10 mg naloxone and were produced either by spray granulation according to Example 1 (Ox/Nal-10) or by extrusion according to Example 2 (Oxy/Nal-Extr). Additionally, a Valoron® N tablet with 100 mg Tilidin and 8 mg Naloxone was used. FIGS. 5A and 5B show different magnifications of scanning electron microscopy pictures of a Ox/Nal-10-tablet with a formulation according to the invention which was produced by spray granulation. FIGS. 6A and 6B show different magnifications of scanning electron microscopy pictures of a Oxy/Nal-Extr-tablets with a formulation according to the invention, which was produced by extrusion. FIGS. 7A and 7B show scanning electron microscopy pictures of the Valoron® N-tablet.

From a comparison of the figures one can clearly see that tablets with a formulation according to the invention have a surface which is substantially finer and more homogeneously structured and which shows fewer cracks than the Valoron® tablet, regardless of whether the tablets have been produced by spray granulation or extrusion. The structural difference is possibly the reason for the different release behaviors of the different preparations.

Example 7—Production of Tablets with Different Oxycodone/Naloxone Amounts in a Non-Swellable Diffusion Matrix by Extrusion The following amounts of the listed components were used for the production of oxycodone/naloxone tablets according to the invention.

| Preparation (designation) | OxN20/1-Extr-A | OxN20/1-Extr-B | OxN20/1-Extr-C | OxN20/10-Extr-A |
|---|---|---|---|---|
| Oxycodone HCl | 20 mg | 20 mg | 20 mg | 20 mg |
| Naloxone HCl | 1 mg | 1 mg | 1 mg | 10 mg |
| Lactose Flow Lac 100 | 58.25 mg | 58.25 mg | 58.25 mg | 49.25 mg |
| Kollidon ® 30 | 6 mg | 6 mg | 6 mg | 6 mg |
| Ethylcellulose | 10 mg | 10 mg | 10 mg | 10 mg |
| Stearly alcohol | 24 mg | 24 mg | 24 mg | 24 mg |
| Talcum | 1.25 mg | 1.25 mg | 1.25 mg | 1.25 mg |
| Mg-Stearate | 2.5 mg | 2.5 mg | 2.5 mg | 2.5 mg |

Extrusion was performed as described above (Example 2) with the following 10 parameters:

| OxN20/1-Extr-A: | temperature: | 55-63° C. |
| | rpm (screw): | 150 rpm |
| | feeding rate: | 1.5 kg/h |
| OxN20/1-Extr-B: | temperature: | 55-63° C. |
| | rpm (screw): | 155 rpm |
| | feeding rate: | 1.5 kg/h |
| OxN20/1-Extr-C: | temperature: | 55-63° C. |
| | rpm (screw): | 1505 rpm |
| | feeding rate: | 1.5 kg/h |
| OxN20/10-Extr-A: | temperature: | 55-63° C. |
| | rpm (screw): | 160 rpm |
| | feeding rate: | 1.75 kg/h |

Tablet production was performed with a common tabletting device with the 10 following parameters:

| OxN20/1-Extr-A: | rpm: | 40 rpm |
| | Pressure power: | 9 kN |
| OxN20/1-Extr-B: | rpm: | 42 rpm |
| | Pressure power: | 8.9 kN |
| OxN20/1-Extr-C: | rpm: | 36 rpm |
| | Pressure power: | 9 kN |
| OxN20/10-Ext-A: | rpm: | 36 rpm |
| | Pressure power: | 7.5 kN |

The release of the active compounds was measured over a time period of 12 hours, applying the Basket Method according to USP at pH 1.3 using HPLC. Tablets OxN20/1-Extr-A, OxN20/1-Extr-B, OxN20/1-Extr-C and OxN20/10-Extr-A were tested.

One recognizes from the values listed in the Table that in the case of a non-swellable diffusion matrix based on ethylcellulose, the release rates of different naloxone amounts, independent of the oxycodone amount, remain substantially equal. Correspondingly, the preparations provide for an independent and invariant release of the active compounds.

| Time  | OxN20/1-Extr-A | | OxN20/1-Extr-B | | OxN20/1-Extr-C | | OxN20/10-Extr-A | |
|---|---|---|---|---|---|---|---|---|
| (min) | Oxy | Nal | Oxy | Nal | Oxy | Nal | Oxy | Nal |
| 0   | 0    | 0    | 0     | 0    | 0     | 0    | 0    | 0    |
| 15  | 21.2 | 25.8 | 21.7  | 21.1 | 19.7  | 19.3 | 23.3 | 24.3 |
| 120 | 56.6 | 53.8 | 58.8  | 57.3 | 57.7  | 56.2 | 64.5 | 66.9 |
| 420 | 87.2 | 84.5 | 94.2  | 92.6 | 93.7  | 91.5 | 92.7 | 96.3 |
| 720 | 99.7 | 96.8 | 100.1 | 98   | 100.6 | 97.5 | 93.6 | 97.4 |

The release values refer to oxycodone or naloxone (line 2) and are given as percentages. The mean value for the release of naloxone at e.g. 420 min is 92.3%. The maximal deviation at 420 min is 7.4%. Oxy and Nal stand for oxycodone and naloxone and indicate the active compound which has been measured.

Thus, once a preparation with the desired release profile has been developed, one can change the amount of the active compounds without significantly changing the release profiles of the active compounds. The preparations comprising different amounts of the active compounds still provide for a sustained, independent an invariant release of the active compounds.

Example 8—Production of Tablets with Oxycodone/Naloxone in a Non-Swellable Diffusion Matrix by Extrusion In the following example it is set out that using formulations according to the present invention, preparations comprising oxycodone and naloxone with particular release behaviors may be obtained.

The following amounts of the listed components were used for the production of oxycodone/naloxone tablets according to the invention.

| Preparation (designation) | OxN20/1-Extr-D | OxN20/1-Extr-E | OxN20/10-Extr-B | OxN20/10-Extr-C | OxN20/10-Extr-D | OxN20/10-Extr-E |
|---|---|---|---|---|---|---|
| oxycodone HCl    | 20 mg    | 20 mg    | 20 mg    | 20 mg    | 20 mg    | 20 mg    |
| naloxone HCl     | 1 mg     | 1 mg     | 10 mg    | 10 mg    | 10 mg    | 10 mg    |
| Lactose Flow Lac 100 | 56.25 mg | 56.25 mg | 54.25 mg | 65.25 mg | 60.25 mg | 55.25    |
| Kollidon ® 30    | 7 mg     | 6 mg     | 6 mg     | 7.25 mg  | 7.25 mg  | 7.25 mg  |
| Ethylcellulose   | 11 mg    | 12 mg    | 10 mg    | 12 mg    | 12 mg    | 12 mg    |
| Stearyl alcohol  | 24 mg    | 24 mg    | 24 mg    | 28.75 mg | 28.75 mg | 28.75 mg |
| Talcum           | 1.25 mg  | 1.25 mg  | 1.25 mg  | 1.25 mg  | 1.25 mg  | 1.25 mg  |
| Mg-Stearate      | 2.5 mg   | 2.5 mg   | 2.5 mg   | 2.5 mg   | 2.5 mg   | 2.5 mg   |

Extrusion was performed as described above (Example 2) with the following parameters:

| | | |
|---|---|---|
| OxN20/1-Extr-D:  | temperature:  | 55-63° C. |
|                  | rpm (screw):  | 150 rpm   |
|                  | feeding rate: | 1.5 kg/h  |
| OxN20/1-Extr-E:  | temperature:  | 55-63° C. |
|                  | rpm (screw):  | 150 rpm   |
|                  | feeding rate: | 1.5 kg/h  |
| OxN20/10-Extr-B: | temperature:  | 55-63° C. |
|                  | rpm (screw):  | 160 rpm   |
|                  | feeding rate: | 1.75 kg/h |
| OxN20/10-Extr-C: | temperature:  | 55-63° C. |
|                  | rpm (screw):  | 160 rpm   |
|                  | feeding rate: | 1.75 kg/h |
| OxN20/10-Extr-D: | temperature:  | 55-63° C. |
|                  | rpm (screw):  | 150 rpm   |
|                  | feeding rate: | 1.5 kg/h  |
| OxN20/10-Extr-E: | temperature:  | 55-63° C. |
|                  | rpm (screw):  | 150 rpm   |
|                  | feeding rate: | 1.5 kg/h  |

Tablet production was performed with a common tabletting device with the following parameters:

| | | |
|---|---|---|
| OxN20/1-Extr-D:  | rpm:            | 39 rpm   |
|                  | Pressure power: | 11 kN    |
| OxN20/1-Extr-E:  | rpm:            | 39 rpm   |
|                  | Pressure power: | 10.5 kN  |
| OxN20/10-Extr-B: | rpm:            | 36 rpm   |
|                  | Pressure power: | 9.5 kN   |
| OxN20/10-Extr-C: | rpm:            | 36 rpm   |
|                  | Pressure power: | 7.8 kN   |
| OxN20/10-Extr-D: | rpm:            | 39 rpm   |
|                  | Pressure power: | 9 kN     |
| OxN20/10-Extr-E: | rpm:            | 39 rpm   |
|                  | Pressure power: | 7.5 kN   |

The release of the active compounds was measured over a time period of 12 hours, applying the Basket Method according to USP at pH 1.2 using HPLC. Tablets Ox.N20/1-Extr-D, OxN20/1-Extr-E, OxN20/10-Extr-B, OxN20/10-Extr-C, OxN20/10-Extr-D and OxN20/10-Extr-E were tested.

| Time | OxN20/1-Extr-D | | OxN20/1-Extr-E | | OxN20/10-Extr-B | | OxN20/10-Extr-C | | OxN20/10-Extr-D | | OxN20/10-Extr-E | |
|---|---|---|---|---|---|---|---|---|---|---|---|---|
| (min) | Oxy | Nal | Oxy | Nal | Oxy | Nal | Oxy | Nal | Oxy | Nal | Oxy | Nal |
| 0 | 0 | 0 | 0 | 0 | 0 | 0 | 0 | 0 | 0 | 0 | 0 | 0 |
| 15 | 16.6 | 16.2 | 17.4 | 17.2 | 26.1 | 26.8 | 21.8 | 21.9 | 18.5 | 18.2 | 18.4 | 18.2 |
| 120 | 47.6 | 46.9 | 49.6 | 49.7 | 71.1 | 73.0 | 61.2 | 61.8 | 52.8 | 52.8 | 53.3 | 53.3 |
| 420 | 82.7 | 84.5 | 84.6 | 85.7 | 94.3 | 96.6 | 93.2 | 94.7 | 86.3 | 86.3 | 87.2 | 88.2 |
| 720 | 95 | 97 | 95.2 | 95.8 | 94.9 | 97.9 | 96.4 | 97.9 | 94.8 | 94.8 | 95.7 | 96.5 |

The release values refer to oxycodone or naloxone (line 2) and are given as percentages. Oxy and Nal stand for oxycodone and naloxone and indicate the active compound which has been measured.

The example shows that preparations with particular release profiles may be produced if ethylcellulose and fatty alcohols are used as the matrix-components that essentially influence the release characteristics of the preparations. Once a preparation with desired release characteristics has been obtained the amount of the active compounds may be changed. The preparations will still provide for a sustained, independent and invariant release behaviour (see example 7).

The invention claimed is:

1. An oral pharmaceutical formulation comprising: about 40 mg to 150 mg of oxycodone or a pharmaceutically acceptable salt thereof; and naloxone or a pharmaceutically acceptable salt thereof; wherein the oxycodone or pharmaceutically acceptable salt thereof and the naloxone or pharmaceutically acceptable salt thereof are present in the pharmaceutical formulation in a weight ratio of 2:1 and are released from the pharmaceutical formulation in a sustained manner.

2. The oral pharmaceutical formulation of claim 1, wherein the oxycodone or pharmaceutically acceptable salt thereof is present in the form of oxycodone hydrochloride.

3. The oral pharmaceutical formulation of claim 1, wherein the naloxone or pharmaceutically acceptable salt thereof is present in the form of naloxone hydrochloride.

4. The oral pharmaceutical formulation of claim 1, wherein the oxycodone or pharmaceutically acceptable salt thereof is present in an amount of about 40 mg.

5. The oral pharmaceutical formulation of claim 1, wherein the oxycodone or pharmaceutically acceptable salt thereof is present in an amount of about 50 mg.

6. The oral pharmaceutical formulation of claim 1, wherein the oxycodone or pharmaceutically acceptable salt thereof is present in an amount of about 80 mg.

7. The oral pharmaceutical formulation of claim 1, wherein the oxycodone or pharmaceutically acceptable salt thereof is present in an amount of 150 mg.

8. The oral pharmaceutical formulation of claim 1, wherein the formulation is in the form of a tablet.

9. The oral pharmaceutical formulation of claim 1, wherein the formulation is formulated to release the oxycodone or pharmaceutically acceptable salt thereof and the naloxone or pharmaceutically acceptable salt thereof over 2 to 24 hours.

10. The oral pharmaceutical formulation of claim 1, wherein the formulation is formulated to release the oxycodone or pharmaceutically acceptable salt thereof and the naloxone or pharmaceutically acceptable salt thereof over 2 to 12 hours.

11. The oral pharmaceutical formulation of claim 1, wherein the formulation is formulated to release about 40% to 80% of the oxycodone or pharmaceutically acceptable salt thereof and the naloxone or pharmaceutically acceptable salt thereof after 2 hours.

12. The oral pharmaceutical formulation of claim 1, wherein the formulation is formulated to release about 85% to 100% of the oxycodone or pharmaceutically acceptable salt thereof and the naloxone or pharmaceutically acceptable salt thereof after 12 hours.

13. The oral pharmaceutical formulation of claim 1, wherein the formulation is formulated to release the oxycodone or pharmaceutically acceptable salt thereof and the naloxone or pharmaceutically acceptable salt thereof such that
   the percent released of the oxycodone or pharmaceutically acceptable salt thereof deviates from the percent released of the naloxone or pharmaceutically acceptable salt by not more than 20% per time unit, or
   the percent released of the naloxone or pharmaceutically acceptable salt thereof deviates from the percent released of the oxycodone or pharmaceutically acceptable salt by not more than 20% per time unit.

14. An oral pharmaceutical formulation comprising:
   oxycodone or a pharmaceutically acceptable salt thereof; and
   about 20 mg to 40 mg of naloxone or a pharmaceutically acceptable salt thereof;
   wherein the oxycodone or pharmaceutically acceptable salt thereof and the naloxone or pharmaceutically acceptable salt thereof are present in the pharmaceutical formulation in a weight ratio of 2:1 and are released from the pharmaceutical formulation in a sustained manner.

15. The oral pharmaceutical formulation of claim 14, wherein the oxycodone or pharmaceutically acceptable salt thereof is present in the form of oxycodone hydrochloride, and the naloxone or pharmaceutically acceptable salt thereof is present in the form of naloxone hydrochloride.

16. The oral pharmaceutical formulation of claim 14, wherein the naloxone or pharmaceutically acceptable salt thereof is present in an amount of about 20 mg.

17. The oral pharmaceutical formulation of claim 14, wherein the naloxone or pharmaceutically acceptable salt thereof is present in an amount of about 30 mg.

18. The oral pharmaceutical formulation of claim 14, wherein the naloxone or pharmaceutically acceptable salt thereof is present in an amount of about 40 mg.

19. The oral pharmaceutical formulation of claim 14, wherein the formulation comprises a sustained release matrix, wherein the sustained release matrix comprises the oxycodone or pharmaceutically acceptable salt thereof and the naloxone or pharmaceutically acceptable salt thereof.

20. A method of treating pain in a subject, wherein the method comprises administering to the subject identified in need thereof the oral pharmaceutical composition of claim 14.

* * * * *